United States Patent [19]
Goffe et al.

[11] Patent Number: 5,683,916
[45] Date of Patent: Nov. 4, 1997

[54] MEMBRANE AFFINITY APPARATUS AND PURIFICATION METHODS RELATED THERETO

[75] Inventors: Randal A. Goffe, Medway; Stephen E. Zale, Marlborough; James L. O'Connor, Chelmsford; Stephen B. Kessler, Princeton, all of Mass.

[73] Assignee: Hemasure Inc., Marlborough, Mass.

[21] Appl. No.: 465,479

[22] Filed: Jun. 5, 1995

Related U.S. Application Data

[63] Continuation of Ser. No. 83,859, Jun. 28, 1993, abandoned, which is a continuation of Ser. No. 265,061, Oct. 31, 1988, abandoned.

[51] Int. Cl.$^6$ ................ G01N 33/549; G01N 33/543
[52] U.S. Cl. ............... 436/535; 210/198.3; 210/500.21; 210/500.23; 210/500.41; 210/638; 210/656; 435/6; 435/180; 435/181; 435/182; 435/287.1; 435/287.2; 435/288.1; 436/161; 436/178; 436/518; 436/531; 436/532; 530/413; 530/417
[58] Field of Search ................ 210/198.3, 500.21, 210/500.23, 500.41, 638, 656; 435/180–182, 6, 287.1, 287.2, 288.1; 436/161, 178, 518, 531, 532, 535; 530/413, 417

[56] References Cited

U.S. PATENT DOCUMENTS

| | | | |
|---|---|---|---|
| 3,947,352 | 3/1976 | Cuatrecasas et al. | 210/692 |
| 3,983,001 | 9/1976 | Cŏupek et al. | 530/413 |
| 3,993,560 | 11/1976 | Halpern. | |
| 4,163,174 | 7/1979 | Gregor | 435/182 |
| 4,252,653 | 2/1981 | Beck et al. | 210/321.3 |
| 4,259,448 | 3/1981 | Nakamura et al. | 435/215 |
| 4,474,690 | 10/1984 | Nylen. | |
| 4,512,896 | 4/1985 | Gershoni | 422/70 X |
| 4,596,660 | 6/1986 | Hou | 210/908 |
| 4,612,119 | 9/1986 | Eguchi | 210/500.23 |
| 4,663,163 | 5/1987 | Hou et al. | 210/635 |
| 4,687,820 | 8/1987 | Hou et al. | 210/656 |
| 4,693,985 | 9/1987 | Degen et al. | 436/532 X |
| 4,721,730 | 1/1988 | Furuyoshi et al. | 210/679 |
| 4,743,373 | 5/1988 | Rai et al. | 210/198.2 |
| 4,758,349 | 7/1988 | Ma | 210/677 |

(List continued on next page.)

FOREIGN PATENT DOCUMENTS

| | | |
|---|---|---|
| 0 095554 A2 | 2/1983 | European Pat. Off.. |
| 0 173500 A1 | 8/1985 | European Pat. Off.. |
| 239079 | 9/1987 | European Pat. Off.. |
| 249932 | 12/1987 | European Pat. Off.. |
| 0483 143 B1 | 6/1994 | European Pat. Off.. |
| 61-90672 | 10/1984 | Japan. |
| WO 88/06899 | 9/1988 | WIPO. |
| WO 89/05876 | 6/1989 | WIPO. |

OTHER PUBLICATIONS

Kesting R.E.; "Synthetic Polymeric Membranes", 2nd Ed., John Wiley & Sons, 1885 pp. 44–61.
STN Accession No.: CA98124j:204952v.
Dialog, Embase No.: 78328717.
Dialog Abstract No.: 0766288.
Dialog, DBA Accession No.: 84–05414.

*Primary Examiner*—Christopher L. Chin
*Attorney, Agent, or Firm*—Pennie & Edmonds LLP

[57] ABSTRACT

A method and apparatus for carrying out affinity purification of a ligate. The method comprising, (a) providing a ligate containing liquid to a first side of at least one porous hollow fiber membrane with a ligand immobilized thereto that binds and separates the ligate from the liquid, (b) withdrawing a first portion of the liquid from the first side of the porous hollow fiber membrane, (c) recirculating the first portion of liquid to the first side of the porous hollow fiber membrane, (d) repeating steps (a) to (c) until a majority of the liquid has flowed through the porous hollow fiber membrane, and (e) providing an elution solution to one side of the porous hollow fiber membrane under a pressure sufficient to cause the elution solution to flow into and through the membrane to effect disassociation of any ligate-ligand bonds wherein any ligate bound to the ligand is eluted with the elution solution.

30 Claims, 12 Drawing Sheets

U.S. PATENT DOCUMENTS

| | | | |
|---|---|---|---|
| 4,780,210 | 10/1988 | Hsia | 210/638 |
| 4,794,002 | 12/1988 | Henis et al. | 427/389.9 |
| 4,806,546 | 2/1989 | Carrico et al. | 435/803 |
| 4,867,934 | 9/1989 | Repetti | |
| 4,885,087 | 12/1989 | Kopf | 210/321.72 |
| 4,919,811 | 4/1990 | Davis | 210/500.41 |
| 4,956,289 | 9/1990 | Wrasidlo et al. | 435/180 |
| 5,045,190 | 9/1991 | Carbonell et al. | 210/502.1 |

HOLLOW-FIBER MEMBRANE AFFINITY SEPARATION STEPS

1: LOAD - FILTRATE ON SHELL SIDE CAN BE RECIRCULATED TO FEED STREAM TO RECLAIM UNBOUND PRODUCT IF NECESSARY.

BROTH RECYCLED

2: WASH - CONDUCTED FROM SHELL SIDE TO EFFICIENTLY REMOVE POTENTIAL PRODUCT CONTAMINANTS FROM THE INTERSTICES OF THE FIBERS.

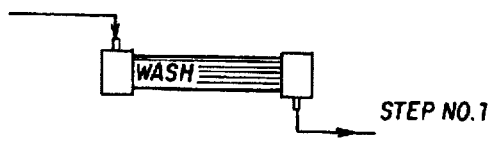
STEP NO. 1

STEP NO. 2

3: ELUTE - CONDUCTED FROM THE SHELL SIDE TO PREVENT PRODUCT LOSSES DUE TO DUE TO DEAD VOLUME EFFECTS.

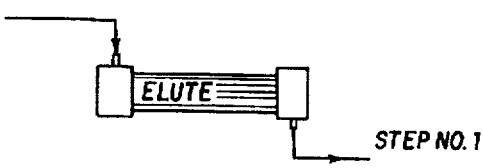
STEP NO. 1

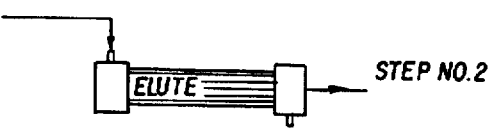
STEP NO. 2

4: REGENERATE - OPERATED IN THE REGULAR CROSS-FLOW FILTRATION MODE.

FIG. 3

EXPERIMENTAL SETUP FOR AFFINITY MEMBRANE MEDIATED PURIFICATION OF FN FROM BLOOD PLASMA.

DOUBLE ANNULAR
CO-EXTRUSION SPINNERETTE

ALTERNATIVE DESIGN FOR DOUBLE
ANNULAR CO-EXTRUSION SPINNERETTE

MEMBRANE AFFINITY APPARATUS AND PURIFICATION METHODS RELATED THERETO

This is a continuation of application Ser. No. 08/083,859, filed Jun. 28, 1993, now abandoned, which is a continuation of application Ser. No. 07/265,061, filed Oct. 31, 1988, now abandoned.

TABLE OF CONTENTS
1.0 Field of the Invention
2.0 Background of the Invention
  2.1 Affinity Separations
  2.2 Factors for Process Design
  2.3 Maximizing Mass Transfer
  2.4 Membrane-Based Affinity Supports
  2.5 Surface Modification of Polymers
    2.5.1 Previous Method for the Modification of Polymer or Membrane Surfaces
  2.6 Prior Method for the Production of Microporous Membranes
  2.7 Spinnerette Assemblies of the Prior Art
3.0 Summary of the Invention
4.0 Brief Description of the Figures
5.0 Detailed Description of the Invention
  5.1 General Apparatus Description
  5.2 General Description of Affinity Membrane Process for Protein Purification
  5.3 Modified Membranes Utilized in Apparatus and Method of their Manufacture
    5.3.1 Membrane and Module Design Considerations
    5.3.2 Modification of Hydrophobic Polymer Surface
    5.3.3 Process for Manufacturing Substantially Isotropic Microporous Membranes
      5.3.3.1 Dope Composition
      5.2.3.2 Flat Sheet Membranes
      5.2.3.3 Improved Co-Extrusion Spinnerette and Production of Hollow Fibers
    5.3.3 Charge-Modified PES Membrane Surfaces
    5.3.4 Preparation of Modules Containing Modified Hollow Fiber Membranes
      5.3.4.1 Immunoaffinity Purification of Factor VIII (FVIII)
    5.3.5 Modification of Commercial Flat Sheet and Hollow Fiber Membranes
  5.4 Membrane Process and Apparatus Specifications
6.0 Examples
  6.1 Membrane Affinity Purification of Fibronectin from Blood Plasma
  6.2 Immunoaffinity Purification of Factor VIII
  6.3 Immunoaffinity Purification of F. VIII from Blood Plasma
  6.4 Protein A Membrane-Mediated Capture of Human IgG
  6.5 Protein A Mediated Capture of a Monoclonal Antibody from Cell Culture Supernatant
  6.6 Protein A membrane mediated Purification of Monoclonal Antibody from Cell culture Supernatant
  6.7 Dope Preparation and Polymer Drying Procedure
    6.7.1 Mixing Procedure
  6.8 Hollow Fiber Spinning of Relatively Isotropic Microporous Membranes Primarily for Affinity Applications
  6.9 Effect of Wash Time and Temperature
  6.10 Modification of Hollow Fiber Membrane
  6.11 Attachment of Anti-Factor IX Monoclonal Antibody to a 1.5 ml Module and Immunopurification of Factor IX

1.0 FIELD OF THE INVENTION

This invention relates to an apparatus and methods for carrying out affinity separation. More specifically, this invention relates to an apparatus which utilizes a membrane in association with a ligand to separate a ligate from a fluid containing the ligate. Also disclosed are methods for carrying out affinity separation in the apparatus.

2.0 BACKGROUND OF THE INVENTION

2.1 Affinity Separations

Of the separation technologies available today, those based on affinity interactions are ever more popular—particularly at the laboratory scale. Affinity separation has become the preferred method for purifying proteins and other biomolecules from complex, biologically derived fluids. *Affinity Chromatography and Biological Recognition*, 1983. I. M. Chaiken, M. Wilchek, and I. Parikh (eds.). Academic Press, New York. Hill, E. A., and Hirtenstein, M. D. 1983. Affinity chromatography: its application to industrial scale processes, pp. 31–66 in *Advances in Biotechnological Processes*. Alan R. Liss, Inc., New York. The key to the method's attractiveness is its unequaled degree of selectivity.

Affinity separations, as they are currently practiced, typically involve the following steps: A solution containing the compound of interest is passed through a column containing a highly specific ligand immobilized on a solid support. As the fluid passes through the column, the desired component binds selectively—and reversibly—to the ligand; most impurities pass unhindered. Any residual impurities are removed by flushing the column with an appropriate buffer solution. The compound, now purified but still bound, is then recovered by passing through the column a solution that disrupts the ligand-binding interaction—by changing ionic strength or pH, for instance.

Many types of molecules can serve as ligands, including antibodies, antigens, enzyme inhibitors, isolated receptors, and more recently, cloned receptors. Bailon, P., Weber, D. V., Keeney, R. F., Fredericks, J. E., Smith, C., Familletti, P. C., and Smart, J. E. 1987, *Receptor-affinity chromatography: a one-step purification for recombinant interleukin-2*. Bio/Technology 5:1195. In contrast, however, the choice of materials to support the ligand has been limited to either agarose gel beads or silica particles. Although both of these materials are quite suitable for laboratory-scale affinity separations, they do not scale-up well. The intrinsic compressibility of agarose gel beads poses severe limitations for engineering efficient process-scale separation systems. Arnold, F. H., Chalmers, J. J., Saunders, M. S. Croughan, M. S., Blanch, H. W., and Wilke, C. R. 1985; A rational approach to the scale-up of affinity chromatography, pp. 113–122 in *Purification of Fermentation Products*, D. LeRoith, J. Shiloach, and T. J. Leahy (eds.), American Chemical Society, Washington, D.C.

Compressibility may be more than a limitation: it has even been considered a major liability if used in process-scale affinity systems. Clonis, Y. D. 1987, *Large-scale affinity chromatography*, Bio/Technology 5:1290. The compression and associated tight packing of an agarose gel bed under typical operating conditions can often seriously compromise the throughput of such systems. Silica supports, which have greater structural rigidity, have provided an alternative to agarose gels. Indeed, silica does minimize compression and allows for the high throughputs necessary for a commercial process system. However, high throughputs are realized only at the expense of high operating pressures. And high operating pressures mean increased costs for capital equipment.

2.2 Factors for Process Design

Realizing the intrinsic material constraints of both agarose gel beads and silica particles, design engineers turned instead to manipulating bed geometry to circumvent the through-put/pressure tradeoff.

Efforts to maximize throughput have resulted in a trend towards shorter, wider beds since, for a given pressure drop across the bed, the throughput is inversely proportional to the bed height. A number of column configurations are now on the market: these range from stacked configurations (a number of short beds are connected in series-parallel combinations) to radial flow arrangements (a short, wide bed is curled up end-to-end upon itself).

The "ideal" column geometry would have an infinitely short bed height (to minimize operating pressures and maximize operating pressures and maximize throughput) and an infinite width (to maximize ligand loading and binding capacity). In reality, a substantially isotropic microporous hollow fiber membrane configuration approaches this ideal quite closely, with "bed heights" in the 300-micron range and large internal surface areas.

However, a key parameter in designing processes for affinity separations and one that has been all but overlooked is ligand utilization. Although some scientists use "ligand loading capacity" to measure the efficiency of an affinity column, in reality it is ligand utilization that determines efficiency.

If the requirements of the system are such that an extended residence time is necessary for a high degree of solute/ligand binding, then the only way this extended residence time can be accomplished, without sacrificing throughput, is by increasing the size of the device. A bigger device requires more ligand. This becomes a particularly important consideration when the ligand is relatively expensive (as for a monoclonal antibody or a receptor); the price of the ligand now becomes a substantial portion of overall purification costs. If residence time can be reduced, the ligand will be used at maximum efficiency.

2.3 Maximizing Mass Transfer

To maximize ligand use within an affinity device, it is necessary to maximize mass transfer. In packed bed affinity columns, mass transfer is limited by the time it takes for solute molecules to diffuse through the interstitial spaces to the ligand itself which resides on the surface or within the pores of gel beads and silica particles. Assuming rapid binding kinetics, the ligand would be used efficiently only if the average time for a solute molecule to diffuse to the ligand ($t_D$) is substantially shorter than its column residence time ($t_c$) (Relation 1). From this, we can define a form of Peclet number, $P^e$. Kessler, S. B., Zale, S. E., and Bratzler, R. L. in 1987, *Affinity device designs for process scale applications*, Presented at the Society for Industrial Microbiology Annual Meeting, Baltimore, Md. Boucher, D. F. and Alves, G. E. 1959, *Dimensionless numbers*, Chem. Eng. Progress 55:55, as in:

$$t_D << t_c \qquad \text{Relation 1}$$

$$Pe = t_D/t_c = (L_D^2/D)/(V_c/Q) \qquad \text{Equation 1}$$

Equation 1 (where D is the diffusion coefficient of the solute of interest) can be used to indicate mass transfer efficiency; the $P^e$ values for high efficiencies are significantly less than unity.

Mass transfer efficiency is highly dependent upon diffusional path length ($L_D$). In a packed bed affinity column, this value is necessarily determined by the mean particle radius, hence the trend towards reduced particle size in conventional affinity supports. Once again, however, there is a trade-off. Improved mass transfer is attained only at the expense of the elevated operating pressures.

Membrane-based separation systems, however, largely alleviate the mass transfer limitations seen with conventional technology. Because solute molecules are convected through the membrane support past the ligand, rather than having to diffuse to a bead or particle to reach the ligand, diffusional path lengths are minimized and mass transfer efficiency increases significantly. However, even in the case of membranes there is a conflict between high capacity and good mass transfer characteristics which necessitate careful membrane design.

In U.S. Pat. No. 4,163,714 issued Aug. 7, 1979, there is described a pressure driven membrane affinity system. In this system the assorted ligate is both adsorbed onto and disassociated from the membrane with the feed liquid, wash and elution solution all being provided to the same surface of the membrane. This process, however, results in the ligate being gradually associated in a somewhat inefficient manner, thereby making it difficult to separate the ligate from the elution solution.

If the rate of ligand/solute association in a particular affinity separation happens to be slower than the rate of solute diffusion, it is conceivable that improving the diffusion characteristics would have no effect on the process efficiency. On the other hand, the association kinetics might.

If one examines the association kinetics of a Sepharose-bound antigen ligand as a model, it is evident that the characteristic reaction time for antibody/antigen association ($t_R$) depends on the concentration of binding sites within the Sepharose bead ($q_m$). The reaction time can be calculated using Equation 2, where $k_1$ is the second order association rate constant and $\theta$ is the fractional saturation of the adsorbent.

$$t_R = 1/k_1 \cdot q_m (1-\theta) \qquad \text{Equation 2}$$

Using Equation 2, Olsen and Yarmush (Olson, W. C., and Yarmush, M. L. 1987, *Electrophoretic elution from monoclonal antibody immunoadsorbents: A theoretical and experimental investigation of controlling parameters*, Biotech. Progress 3:177) have calculated that bovine serum albumin (BSA) binds to monoclonal antibody-coated Sepharose beads on the order of five seconds. Conversely, the average time required for BSA to diffuse to the bead's surface is much longer—41 seconds. This time is given by $L_D^2/D$ (see Equation 1) where $L_D$ is the mean bead radius ($5 \times 10^{-3}$ cm) and D is the diffusion coefficient for BSA ($6 \times 10^{-7}$ cm$^2$/sec). The average diffusion time is almost an order of magnitude greater than that for solute/ligand association. Thus, conventional affinity separations are diffusion-limited for this system: for large-scale processes, this is inefficient.

2.4 Membrane-Based Affinity Supports

In the search for superior affinity substrates it was inevitable that membranes would emerge as an alternative to packed columns. Until now, however, the advancement of membrane-based affinity purification technology has been limited by the availability of systematically designed membranes for this purpose. Consequently, conventional flat sheet filters have been investigated for use as affinity separators by Gregor (U.S. Pat. No. 4,163,714) and Degan et al (U.S. Pat. No. 4,693,985).

Gregor (U.S. Pat. No. 4,163,714) claims ultrafilters (UF) with an average pore size of about 15 to 200 Angstrom. Current technology for producing UF membranes invariably creates a skinned anisotropic structure. While the relatively small pore size is advantageous due to a high internal surface area, protein sieving during the binding (or loading) step in an affinity process would severely limit the utility of such membranes. Fouling and plugging of the membrane occurs very soon after a pressure is applied to the ligate containing fluid.

One method which has been employed in cleaning and unplugging ultrafilters is backflushing (or back-washing). This is a process whereby filtrate is forced back across the filter in the reverse direction. After a few years of using backflushing the frequency of its use has dramatically declined in recent years, due in part to catastrophic membrane failure linked with this practice. Backflushing (often at higher pressures than those at which the UF step was carried out), frequently results in:

delamination of the skin region of the membrane from the matrix region;

ruptures (i.e. splits and tears) in the entire membrane wall;

complete and irreversible plugging, as trapped material is unable to pass through the anisotropic matrix in the reverse direction through pores of ever decreasing size.

Hollow fiber membranes are particularly susceptible to damage during backflushing (and the stresses of star-up/ shut-down cycles) because they are self supporting. Flat sheet membranes usually have porous (hydrophobic) backing material to provide mechanical support.

U.S. Pat. No. 4,693,985 describes flat sheet polyamide membranes for affinity applications. These are microporous, skinless membranes with pore diameter of <0.1 to >0.45 µm. They represent a major improvement over UF flat sheet membranes, but are still limited by being difficult to configure in a device (as they are not self supporting). Also, high surface area/low dead volume devices become increasingly difficult to design. In U.S. Pat. No. 4,693,985 pleated filter is described as the best available configuration for packaging flat sheet membrane in a high-surface-area configuration.

The ideal membrane configuration for downstream processing is a hollow fiber for the following reasons:

the high surface-area-to-dead volume which can be achieved per device; and, there are fluid management advantages when feed streams are delivered down the lumen of a fiber.

Stimpson, D. E. ACS Poller Preprints, Vol. 27, No. 2, pg424 (September 1986) studied anisotropic hollow fiber membranes over a wide pore size range as affinity supports and concluded that pores in the size range of about 0.1 µm are preferred for achieving the best compromise between surface area and pore size.

2.5 Surface Modification of Polymers

Synthetic pollers and engineering plastics have long been prominent in the manufacturing industry for their excellent processability and bulk physical properties. Most pollers exhibit desirable physical properties such as thermal and long-term stability, resistance to radiation, wear, abrasion, chemical solvents, and low toxicity. Most polymers also possess good mechanical strength while others demonstrate useful electrical properties. Synthetic materials are in abundance today and are used in all sorts of articles of manufacture from infant bottles and liners to automobile bodies and mechanical parts.

Depending on the end use, however, most engineering polymers exhibit undesirable properties at the polymer surface or interface. Specifically, the surfaces of articles manufactured from the great majority of synthetic engineering plastics are hydrophobic, non-wettable, of low biocompatibility, and they exhibit unacceptable nonspecific protein binding characteristics. Consequently, research workers in the polymer art have sought ways of modifying the surface properties and characteristics of synthetic materials to better suit their anticipated application. This effort has been particularly keen in the biocompatible polymer and membrane art where the surface properties of the membrane are extremely important in determining the usefulness and efficiency of a particular filtration, dialysis, separation, or purification process.

2.5.1 Previous Methods For The Modification Of Polymer Or Membrane Surfaces

A classical method in use by many workers for modifying or derivatizing polymer surfaces involves the introduction of a co-monomer bearing desirable functional groups to the monomer precursor of the primary hydrophobic engineering polymer. This method necessarily results in a copolymer whose backbone is substantially different from the homopolymer and frequently provides a material with less than optimum performance characteristics. This technique is illustrated by the work of Gregor et al. (*J. Applied Polymer Sci.* 1985, 30, 1113–1132; U.S. Pat. No. 4,705,753).

A more basic approach uses a physical blend of polymers, one of which is the so-called "functional" polymer whose desirable properties and pendant functional groups will hopefully be manifest at the bulk polymer interface or, in the case where the polymer has been made into an article of manufacture (e.g., a membrane), at that article's surface. This technique, besides invariably producing a different material, performance-wise, also suffers from limitations involving the physical compatibility of the two types of polymers. Few pairs of polymers are sufficiently compatible to be blended successfully. In this respect, even the molecular weight distribution of one of the components may play a critical role. Even after a suitable pair has been found, the distribution of the functional polymer component over the polymer surface is hard to predict or control. Moreover, such blends are susceptible to phase separation resulting in the removal of the functional component over the course of ordinary use. A number of issued patents describe a variety of blending techniques (See, for example, U.S. Pat. No. 3,629,170, assigned to Uniroyal; U.S. Pat. No. 3,781,381, assigned to Union Carbide; and U.S. Pat. No. 4,387,187, assigned to ICI). A variation involving an additional crosslinking step is discussed in U.S. Pat. No. 4,596,858 issued to Gregor and an article by Gryte et al. published in the *J. Applied Polymer Sci.* 1979, 23, 2611–2625.

Another method seeks to graft a second polymer onto the surface of the engineering polymer (i.e., on the surface of the manufactured article). Such a method requires polymerizing the monomer precursor of the second polymer and then irradiating the engineering polymer surface with gamma, electron beam, or ultraviolet radiation. British Patent No. 801,479, for instance, describes a method in which a coating material is applied onto a structural surface which is then exposed to charged particle radiation to initiate bonding between the two materials. A variation of this process is outlined in another United Kingdom Patent (No. 839,483) in which the bulk polymer is first subjected to ionizing radiation to activate the structural surface and then treated with a dissimilar organic coating material. Such radiation treatment can penetrate the materials to a significant depth and is detrimental to their structural integrity. High energy radiation can precipitate polymer degradation and chain scission.

Yet another alternative is the so-called "composite" or multilayer approach. The strategy behind this basic approach seeks to preserve the bulk properties of the membrane or other article of manufacture and its primary polymer component while introducing the desired interfacial or surface characteristics via a modifying agent which is "layered" onto the material's surface. The means for such a "layering" are varied but not at all straightforward. In practice, the composite approach, although potentially the most attractive, is characterized by a tenuous, weak link at the surface of the bulk polymer and the modifying agent. This instability is particularly apparent where the two materials are simply held together by adsorptive forces. For example, U.S. Pat. Nos. 4,413,074 and 4,432,875, both to Wrasidlo et al., describe a procedure whereby a modifying agent in the form of a surfactant or a cellulose derivative is baked onto a membrane surface in the presence of a perfluorocarbon surfactant. The interaction is weak and the coating can be washed away with an appropriate solvent. Another example of an adsorptive coating is described in European Application 0 221 046 to Henis et al. Although this reference claims that the surface modification is "irreversible" it is, in fact, stable only under conditions which are similar to the initial surface treatment.

A purportedly stronger binding can be achieved by polymerizing a monomer over the bulk polymer surface and then crosslinking the resulting second polymer in situ. This method is described in U.S. Pat. No. 4,618,533 issued to Steuck. The mechanical separation of the two layers remains a possibility, however. In a very drastic method, U.S. Pat. No. 4,340,482 describes a process in which the chemical grafting of an amino acid onto the surface of a preformed poly(vinylidene difluoride) membrane is purportedly achieved after heating the membrane in a solution of 57% glycine, 23% sodium hydroxide, and 20% water at 120° C. up to an hour and 15 minutes. Details of the chemistry of this process are lacking. Such severe reaction conditions undoubtedly introduce some type of reactive functional group onto the backbone of the hydrophobic polymer. The newly introduced functional group or groups may then combine with the substrate or reagent via an unknown mechanism to provide the "grafted" amino acid moieties. The desirability and utility of exposing manufactured articles to such corrosive conditions, as well as the generality and versatility of the described procedure, is highly questionable. Other known methods suffer from the same general drawback and need for the initial introduction of reactive functional groups to the hydrophobic polymer surface. (See, for example, Manaka and Tomioka, *J. Applied Polymer Sci.* 1965, 9, 3635; Iwakura et al. *J. Polymer Sci.* 1963, C4, 673).

A series of U.S. Pat. Nos. 4,473,474, 4,473,475, and 4,673,504, describes a method for the charge modification of a hydrophilic wettable membrane surface which utilizes crosslinking agents to form a covalent bond with the "hydroxyl, carboxyl, and primary and secondary amines, which are on the hydrophilic microporous membrane and the cationic charge modifying agent." Although these patents state that a covalent bond may form between amino and carboxyl groups on the surface of the preferred nylon 66 (a polyhexamethylene adipamide) membrane and an epoxy group of the crosslinking agent, they fail to disclose the source and origin of these functional groups and seem to suggest that hydroxyl, carboxyl, and amino groups are simply present on all hydrophilic surfaces including the nylon 66. In fact, polyamides cannot contain hydroxyl functional groups. All three patents expressly state that such hydrophilicity is a necessary element of that invention and the most recently issued patent states, again expressly, that hydrophobic polymer membranes are not amenable to charge modification by the methods of that invention. U.S. Pat. Nos. 4,711,793 and 4,708,803 issued to Ostreicher et al. relate to the same subject matter.

U.S. Patents recently issued to Barnes et al. (U.S. Pat. Nos. 4,743,418 and 4,737,291) and European Patent Application 0 066 814 address a process for using 1,4-butanediol diglycidylether, specifically as a crosslinking agent for modifying the charge of a microporous nylon membrane. Again, these references fail to appreciate or teach the origin and nature of the "hydrophilic" functional groups on the membrane surface.

In U.S. Pat. No. 4,693,985, Degen et al. disclose the covalent binding of a macromolecule to the surface of polyamide membranes. Similar to the disclosures of Barnes, supra, the technique is limited to hydrophilic nylons. The preferred membranes comprise undisclosed surface-modifying polymers which are apparently simply adsorbed on the membrane surface, the polyamide polymer itself, and a supporting polymer. The teachings of this patent would perpetuate the prevailing thinking that polyamide polymers are "reactive and functionalizable" while hydrophobic polymers such as polysulfone are simply "inert" and unreactive.

Thus, there remains a need for the covalent derivatization or modification of hydrophobic polymer surfaces, especially the surfaces of articles manufactured therefrom, under relatively mild reaction conditions. Further, it would be most advantageous if such a modification could be performed under heterogeneous conditions in which the hydrophobic polymer material is first manufactured and processed to exploit its desirable engineering properties and then exposed to a treatment which hopes to modify the surface properties of the preformed article without altering its gross structural characteristics.

2.6 Prior Methods For The Production Of Microporous Membranes

In the specialized area of membrane art, the current methods for producing microporous membranes generally result in skinned anisotropic structures characterized by wide variations in pore sizes from the outer to the inner portions of the membrane. In particular, the production of isotropic hollow fiber membranes has been hampered by prevailing biases in the art and by existing extrusion methods, over and above the general manufacturing techniques.

In the first place, materials or polymers used for manufacturing membranes have generally been classified, as already stated above, into two general groups: reactive or hydrophilic versus inert (See, for example, Cabasso, L in "Membranes," *Encyclopedia of Polymer Science and Eng.,* 1987, 9, 509–579, by Wiley Interscience Publication; Kesting, R. E., *Synthetic Polymeric Membranes* 1985, 2d Ed., Wiley; Pusch, W. and Walch, A., *Angew. Chem. Int. Ed. Engl.* 1982, 21(9), 660–685). Examples of the former group are either intrinsically hydrophilic or can be readily modified to achieve hydrophilicity. High hydrophilicity minimizes the nonspecific binding of proteins to the polymer surface. The main drawback with intrinsically hydrophilic membranes, especially those made from materials such as cellulose, is their limited mechanical and thermal properties. On the other hand, membranes belonging to the latter "inert" group, while possessing superior physical, thermal and chemical resistance properties, are extremely hydrophobic and are thus prone to nonspecific binding of proteins and membrane fouling or plugging.

As a reactive/hydrophilic membrane material, cellulose has been widely used in many of its forms but has some severe drawbacks. These drawbacks include limited pH and chemical resistance (e.g., to chlorine-containing sanitizing agents) and a general lack of requisite physical properties in many applications (See, Kesting, *Syn. Polym. Memb.*, supra).

Polysulfone (PS) is the most widely used polymer type in ultrafiltration (UF) membranes by virtue of its relative versatility, both in terms of physical/chemical properties and processability to produce a wide variety of structures and pore sizes (i.e., with molecular weight cutoffs, MWc, from about 2,000 kD to about 1 kD). Polysulfones have only become an important polymer for the construction of microfiltration (MF) membranes in recent years. Such MF membranes are becoming more numerous in flat sheet form but are still fairly rare in hollow fiber form. Generally speaking, however, polysulfone membranes tend to foul readily and methods for covalently modifying these membrane surfaces have not been developed. Furthermore, these membranes are invariably of the anisotropic variety.

Traditionally, workers in the art have to take into account the pore size range of interest in selecting the membrane polymer. It is believed that certain polymers are more readily processed to make membranes in certain pore-size ranges than others (See, Kesting, *Syn. Polym. Memb.*, supra). Workers in the field such as Strathmann, et al., *Desalination* 1977, 21, 241–255 and *Desalination* 1975, 16, 179–203; Tanny, et al., *J. Appl. Polym. Sci.* 1974, 18, 2149–2163; Koenhen, D. M., et al., *J. Appl. Polym. Sci.* 1977, 21, 199–215; Broens, L., et al., *Desalination* 1977, 22, 205–219; Altena, F. W. and Smolders, C. A., *J. Polym. Sci.: Polymer Symposium* 1981, 69, 1–10; Broens, L., et al., *Desalination* 1980, 32, 33–45; Bokhorst, H. et al., *Desalination* 1981, 38, 349–360; Wijmans, J. G., et al., *J. Memb. Sci.* 1983, 14, 263–274; and Kesting have headed efforts toward a greater understanding of the mechanism of membrane formation and the ways of manipulating structural properties. It has generally been accepted in the field of membrane processing that many key manufacturing parameters have to be changed and tediously reoptimized in going from a flat sheet formulation to a hollow fiber product. Progress, has thus been slow, particularly with respect to the production of isotropic microporous hollow fiber membranes.

Others have pursued the use of blends consisting of hydrophilic and hydrophobic polymers as dopes for preparing membranes (See, Cabasso, I. *Encyclopedia of Polymer Science and Eng.*, supra; Pusch, W. and Walch, A., *Angew. Chem. Int. Ed. Engl.*, supra). Their primary goal has been to use hydrophilic polymers as processing aids; i.e., the hydrophilic polymers are used to increase the viscosity of the dope. Extraction steps used to remove the hydrophilic component, during and after the coagulation process, enhances both the pore density and range of pore sizes attainable. Consequently, these references generally avoid very high molecular weight hydrophilic polymers as blend components because these polymers have a greater tendency to be entrapped in the membrane matrix. Furthermore, the membrane technology literature teaches that, as the molecular weight of a hydrophilic additive increases, especially to the 100,000 range and above, the pore size obtained in the final membrane decreases dramatically (See, Cabasso, I. et al., *J. Appl. Polym. Sci.* 1976, 20, 2377–2394; Nguyen, Q. T. et al., *J. Mem Sci.* 1985, 22, 245–255). For example, Cabasso has shown that by increasing the molecular weight (MW) of polyvinylpyrrolidone (PVP) from 10,000 to 40,000 in an experimental PS/PVP blend, the water permeability (Lp) of the resulting hollow fiber is reduced by a factor of five. Furthermore, the initial modulus and tensile strength also suffer. These results suggest that the PVP is retained in the final membrane as the molecular weight is increased. Apparently, the phenomenon of chain entanglement becomes more important as the molecular weight of a water-soluble polymer additive in the blend increases. Thus the high molecular weight additive is less readily extracted and the density of the final membrane increases, preventing the easy passage of water.

A hollow fiber manufacturing process has also been described (See, Cabasso, I. et al., *J. Appl. Polym. Sci.* supra) which employs optically clear (i.e., single phase) dopes made from PS blended with PVP or polyethylene glycol (PEG) (MW=600) dissolved in either dimethylformamide or dimethylacetamide. This reference emphasizes that these dopes do not exhibit any cloud point behavior, not even, the typical upper critical solution temperature (UCST) observed when nonsolvent is titrated into a polymer/solvent mixture. Instead, these clear dopes, when contacted with nonsolvent, become phase separated with the inward diffusion of nonsolvent. Researchers speculate that the size of the resulting solvent/PVP-rich domains are probably dictated by the thermodynamic phase relationships and by the kinetics of the phase separation (See, Cabasso, I. et al., *J. Appl. Polym. Sci.* 1977, 21, 165–180). These observations are essentially consistent with the findings reported by others (See, Kesting, *Syn. Polym. Memb.*, supra; Kamide, K. and Manabe, S., *Material Science of Synthetic Membranes, ACS Symposium Series* 1985, 269 197–228, Lloyd, D. R., Ed.).

Where very high molecular weight hydrophilic polymers (e.g., poly(ethylene oxide) (PEO), at 4 to 5 million MW) have been blended with polysulfone-type polymers, the intent has been to take advantage of the compatibility between the blended polymers and to retain the hydrophilic polymer in a homogeneously blended transparent film (See, U.S. Pat. No. 4,387,187 and EP 37,181 to Newton and assigned to Imperial Chemical Industries, Ltd.). As disclosed in U.S. Pat. No. 4,387,187, such PES/PEO films or semipermeable membranes are prepared mainly by solvent evaporation, with a leaching step to remove remaining solvent from the already formed film. The degree of porosity attained in such a dense membrane is expected to exclude the permeation of molecules much larger than about 1,000 molecular weight. However, due to the retention of PEO in the final structure there would be some hydrophilicity imparted to the membrane.

When using hydrophilic polymers as processing aids the limitation encountered is that of compatibility. In general, low molecular weight polymers can be loaded into dopes at much higher concentrations (See, Japanese Patent No. 57,035,906). This Japanese patent teaches one how to achieve the maximum possible loading of PEG into a homogeneous dope for membrane casting as a function of molecular weight. PEG molecules above 100,000 MW is specifically excluded.

Similarly, Klein and Smith (U.S. Pat. No. 4,051,300) teach the use of low molecular weight PVP (average molecular weight of at least 2,000) in a blend solution with polysulfone to achieve high dope viscosities for hollow fiber manufacture. The weight ratio of polysulfone to PVP is specified to be no less than 0.5 and no greater than 55. Thus, the relatively low molecular weight hydrophilic polymer additive (so-called, "non-solvent" by Klein and Smith) is used in sufficient quantities to serve as a processing aid. The amount of processing aid is restricted to ensure that:

(i) the dope does not exhibit a phase boundary under normal process conditions, e.g., temperature (Cabasso, I. et al., *J. Appl. Polym. Sci.* supra); and (ii) PVP is not retained in the hollow fiber to reduce either the void volume (or rather the porosity) of the final membrane, or the hydraulic permeability (Lp) and pore size.

Membrane forming PS/PVP dopes of Cabasso (Cabasso, I. et al., *J. Appl. Polym. Sci.* supra) and Klein and Smith (U.S. Pat. No. 4,051,300) require contact with a nonsolvent in either the vapor or liquid phase to undergo phase separation. Under these circumstances, the relative rates of diffusion of nonsolvent into the dope and solvent out of the dope control the process of phase separation in these systems. The nonsolvent employed to induce phase separation causes precipitation of the polysulfone while dissolving and extracting the PVP from the polysulfone fiber as it is being formed.

Relying solely on quenching a dope solution with a nonsolvent frequently gives rise to the formation of a skinned highly anisotropic structure due in part to the limitations imposed by inefficient or slow mass transfer. Greater rates of diffusion of nonsolvent molecules through the dope composition may sometimes be achieved by dissolving smaller amounts of solids in the dope. Quenching these low solids dopes in solvent/non-solvent mixtures helps to overcome skin formation and anisotropy. However, the resulting membranes, though more isotropic, are frequently weak and are not self-supporting. This slow diffusion process of the prior art gives smaller pores near the membrane surface which first comes into contact with the nonsolvent and progressively larger pores deeper into the membrane matrix.

In contrast to the nonsolvent induced liquid/solid phase separation for preparing essentially anisotropic microporous membranes, Castro (U.S. Pat. No. 4,247,498) has exploited thermal phase inversion (i.e., liquid/liquid phase separation brought about by temperature changes) in the preparation of isotropic microporous membranes. Thermal phase inversion, as it is currently practiced, requires a polymer melt and a compatible liquid to give a homogeneous solution in which the polymer is solubilized in the poor solvent. Subsequent cooling of these melts results in the precipitation of the polymer. The structure is thus "frozen" by the cooling process.

Different methods for spinning fibers are known in the art. These include dry-wet spinning, in which there exists an air gap between the extrusion device or spinnerette and the quench bath, and wet-jet spinning (See, Cabasso, I. *Encyclopedia of Chem. Tech.* 3rd Edition, Vol. 12, p. 501). In wet-jet spinning the spinnerette is submerged in the quench bath so that there is a zero air gap. When powerful solvents are employed in the quench bath the plasticizing effect on newly formed fiber can limit spinnability.

2.7 Spinnerette Assemblies Of The Prior Art

Present spinnerette assemblies for hollow fiber manufacturing, are wholly inadequate and inflexible for the production of substantially isotropic microporous membranes. The extrusion dies currently in use do not provide the degree of control over the pore structure and pore-size distribution of the resulting microporous hollow fibers that one would wish to have. Typical tube-in-orifice spinneretres are described in U.S. Pat. Nos. 4,198,363 (Noel, G. et al.) and 4,229,154 (Chaban and Hawkins); in Borneman, Z. et al. *Proceedings*, 4th British Oxygen Company Conference, September 1986, p. 145–157; and in Aptel, P. et al. *J. Memb. Sci.* 1985, 22, 199–215. Spinnerette face plate configurations are further disclosed in an article by Cabasso in "Hollow Fiber Membranes," *Encyclopedia of Chem. Tech.*, 3rd Edition, Vol. 12, p. 499, Kirth-Othmer, Eds.

Numerous other spinnerette assemblies or extrusion dies are described elsewhere. Among these are U.S. Pat. Nos. 4,370,114 (for the production of multi-cored filaments), 1,541,528 (a device for extruding tubing, not hollow fibers), 2,574,555 (double-annular face plate but apparently no central hollow bore), and 3,321,803 (die for coating a metallic pipe). Still other devices are disclosed in U.S. Pat. Nos. 3,121,254 (mentions inert gas in hollow bore), 3,357,051 (for extrusion of double-walled tubes), 3,690,806 (device with internal components useful for reverse-flow and adjustable chock applications), and 3,716,317 (device for spinning filaments from two polymer streams).

A very recent spinnerette assembly, described in U.S. Pat. No. 4,493,629 (the '629 patent), is a modular unit designed for the co-extrusion of three fluids during hollow fiber manufacture and features a tangential entry port. There are two key factors which make this prior device poorly suited for manufacturing substantially isotropic structures:

(1) The '629 patent describes a spinnerette with only one annulus emerging from the face of the spinnerette (i.e., the surface of the device from which the extruded fiber emerges). Thus, fluids within the body of the device will have a tendency to mix before emerging from the spinnerette as a hollow fiber. The extent of mixing is a function of the relative viscosities and relative flow rates. Therefore, two of the three streams entering the device cannot be varied independent of each other over a significant range of flow.

(2) The plurality of ports in the annular spacer described in FIGS. 4 and 5 of the '629 patent is cumbersome. Moreover, the uniformity of the overall flow, via this divided flow-path, is a direct function of the dimensions of each and every port. Problems arise when delicate control of low, and/or, vastly different flow rates are required. Similarly, difficulties are encountered when there are significant differences in viscosity for the two fluid streams which are forced to emerge through the single annular space.

It is, therefore, an object of the present invention to provide a membrane-based affinity system which improves the efficiencies of mass transfer and ligand use and which is amenable to scale-up.

It is an additional object of the present invention to provide an apparatus which has a processing capability equivalent to that of a conventional, 24-column agarose-based affinity system.

It is a further object of this invention to provide an apparatus whose high throughput flow rate and efficient ligand use permit rapid bind/elute cycle times.

It is also an object of this invention to provide a membrane apparatus whose small volume and preferred mode of elution permits product concentration.

3.0 SUMMARY OF THE INVENTION

The apparatus of this invention is a cross flow, hollow fiber affinity membrane system for separation of high value products, such as therapeutic proteins. The central feature of the system is a substantially isostropic microporous hollow fiber membrane designed so as to optimize loading capacity and low dead volume while achieving high mass transfer rates. A large scale system having one 600 ml module is designed to process up to 10,000 liters of cell culture harvest per week. Multiple affinity systems or modules can be run in parallel in order to process even larger quantities of feed material.

The adsorption (or loading) is accomplished by recycling the fluid through the fiber lumen at high recycle rates. A fraction (typically 20%) of the recycle flow permeates the hollow fiber membrane. A highly, specific ligand is immobilized within the membranes porous structure. As the fluid passes through the membrane, the desired component i.e. ligate or target molecule binds selectively—and reversibly—to the ligand; most impurities pass unhindered.

After the adsorption of the ligate, the fibers are washed with a buffer solution, to remove all nonbound impurities. This is accomplished by first washing the shell and then flushing backwards through the membrane to the lumen. The spent wash buffer is routed to drain.

The wash is followed by product elution. A buffer which inhibits or competes with the attraction of the ligand to the product is preferentially, but not limited to being washed through the shell and then backwards through the membrane to the lumen. Optionally, elution can be accomplished in the same manner as the loading step. The presence of product is indicated by a UV adsorption peak, the product is directed to a holding reservoir.

When the elution is complete, the membrane is regenerated by a third buffer that restores the membrane to the initial conditions. This is also conducted through the shell, followed by flushing backwards through the membrane to the lumen. The system is now ready to repeat the cycle.

The apparatus is designed to meet criteria such as high volumetric throughput, high reliability, ease of scale-up, high selectivity and high product yield. The high volumetric throughput is accomplished by high filtrate flow rates enabled by the unique low pressure drop characteristic of the membrane process, but more particularly, by the substantially isotropic, micron pore size, microporous hollow fiber membrane of this invention.

Generally stated, this invention comprises an apparatus for carrying out an affinity separation process comprising:
 (a) a porous isotropic hollow fiber membrane in association with a ligand;
 (b) means for enclosing said porous isotropic hollow fiber membrane;
 (c) a means for providing a first fluid into said enclosure means on one side of said porous isotropic hollow fiber membrane;
 (d) an exit means for directing into a container a fluid present on the opposite side of said membrane than where said first fluid was provided into said enclosure means.

In addition, this invention comprises an apparatus for carrying out an affinity separation process comprising:
 (a) a porous hollow fiber membrane with a mean pore size of at least about 0.20 µm in association with a ligand;
 (b) means for enclosing said porous hollow fiber membrane;
 (c) a means for providing a first fluid into said enclosure means on one side of said porous hollow fiber membrane;
 (d) an exit means for directing into a container a fluid present on the opposite side of said membrane than where said first fluid was provided into said enclosure means.

Generally stated, the membrane of this apparatus may have its interfacial surface derivatized by:
 (a) contacting said membrane with a solution comprising a nonsolubilizing solvent and a linker moiety capable of covalently bridging said membrane to a ligand, which ligand has a plurality of functional groups and is capable of exhibiting the desired interfacial characteristics, for a length of time sufficient to form a covalent bond between a chain end of the polymer comprising said membrane and said linker moiety to form a pendant linker moiety;
 (b) contacting the membrane of step (a) with a solution comprising a nonsolubilizing solvent and said ligand, for a length of time sufficient to form a covalent bond between a functional group of said ligand and said pendant linker moiety, to provide a product membrane with derivatized interfacial characteristics.

Both of the above apparatus may further comprise a second exit means for directing said first fluid into a second container. In addition, both of said apparatus may further comprise a second means for providing a second fluid into said enclosure means on the opposite side of said membrane than said first fluid is provided. Furthermore, this second means for providing may be a reversible pump capable of withdrawing a fluid or regulating the exit means fluid from said enclosure means. In addition, the exit means of element (d) may be closed.

The apparatus of this invention may also comprise:
 (a) a porous membrane in association with a ligand;
 (b) means for enclosing said porous membrane;
 (c) a means for providing a first fluid into said enclosure means on one side of said porous membrane;
 (d) an exit means for directing into a container a fluid present on the opposite side of said membrane than where said first fluid was provided into said enclosure means and;
 (e) a second exit means for directing said first fluid into a second container.

In addition, said apparatus may further comprise a second means for providing a second fluid into said enclosure means on the opposite side of said membrane than said first fluid is provided; and, also, if desired, wherein said second means for providing is a reversible pump capable of withdrawing a fluid or regulating the exit of a fluid from said enclosure means; and further, if desired, wherein said exit means of element (d) is closed; and finally said membrane may be a flat sheet. The flat sheet may further comprise (a) polyethersulfone as the primary hydrophobic polymer component having functionalizable phenolic chain ends; (b) hydroxyalkylcellulose having hydroxyl functional groups; and (c) a linker moiety selected from the group consisting of ethylene glycol diglycidyl ether, 1,4-butanediol diglycidyl ether, epichlorohydrin, and chloroacetic acid, which linker moiety is able to covalently bridge a phenolic chain end of said polyethersulfone with at least one hydroxyl group of said hydroxyalkylcellulose.

Furthermore, this invention comprises the following methods for carrying out affinity purification of a ligate in a membrane system.

I. (a) providing a ligate containing feed liquid to a porous membrane associated with a ligand to said ligate, said feed liquid to flow tangentially across an exterior surface of said membrane and the remainder of said fluid being caused to flow into and through said porous membrane whereby said ligate present in said feed liquid binds to said ligand and is thereby separated from said feed liquid;

(b) washing said membrane with a buffer solution;

(c) providing an elution solution to one side of said membrane under sufficient pressure to cause said elution solution to flow into and through said membrane and to cause the disassociation of any ligate-ligand bonds formed in step (a) whereby any ligate bound to said ligand is eluted with said elution solution;

(d) separating said ligate in a purified form from said elution solution.

II. (a) providing a ligate containing feed liquid to a porous membrane associated with a ligand to said ligate, said feed liquid being under a pressure sufficient to cause said feed liquid to flow into and through said porous membrane whereby said ligate present in said feed liquid binds to said ligand and is thereby separated from said feed liquid;

(b) washing said membrane with a buffer solution;

(c) providing an elution solution to the opposite side of said membrane than where the feed liquid is provided, under sufficient pressure to cause said elution solution to flow into and through said membrane and to cause the disassociation of any ligate-ligand bonds formed in step (a) whereby any ligate bound to said ligand is eluted with said elution solution;

(d) separating said ligate in a purified form from said elution solution.

III. (a) providing a ligate containing feed liquid to a porous membrane associated with a ligand to said ligate, said feed liquids being under a pressure sufficient to cause a portion of said feed liquid to flow tangentially across an exterior surface of said membrane and the remainder of said fluid being caused to flow into and through said porous membrane whereby said ligate present in said feed liquid binds to said ligand and is thereby separated from said feed liquid;

(b) washing said membrane with a buffer solution;

(c) providing an elution solution to the opposite side of said membrane than where the feed liquid is provided, under sufficient pressure to cause said elution solution to flow into and through said membrane and to cause the disassociation of any ligate-ligand bonds formed in step (a) whereby any ligate bound to said ligand is eluted with said elution solution;

(d) separating said ligate in a purified form from said elution solution.

This invention also relates to the methods being used to carry out affinity purification of Factor VIII with a monoclonal antibody to Factor VIII. Fibronectin with porcine gelatin; Factor IX with monoclonal antibody to Factor IX and IgG with Protein A.

The present invention discloses a process for modifying a polymer or structural surface which takes advantage of the functionalizable chain ends of the polymer. The process is carried out under heterogeneous conditions preferably on a polymer which has been preformed into an article of manufacture. Thus, by allowing a covalent bond to form between the functionalizable polymer chain end which is available at the polymer surface and a linker molecule which is capable of serving as a covalent bridge, a ligand or a macromolecule, which is capable of altering the interfacial or surface properties of the polymer, may then be introduced over substantially all the interfacial boundaries of the polymer. The process disclosed is particularly effective for the modification of surfaces of articles manufactured from hydrophobic polymers, although materials made from any polymer with functionalizable chain ends are equally susceptible to modification by the same methods.

The present invention involves the surface modification of membranes comprised of hydrophobic polymeric materials. Thus a membrane produced from polyethersulfone, a hydrophobic engineering material with desirable processing characteristics and useful bulk properties but which undesirably binds proteins nonspecifically by adsorption, can be derivatized or modified covalently by utilizing the phenolic end group present in each polymer chain. In those cases where the polymer end groups are less reactive, these chain ends may be converted to more reactive functional groups by a suitable reagent (See, for example, the conversion of terminal chloride groups to terminal hydroxyl groups in FIG. 1 of copending application of Azad and Goffe entitled "Process for the Covalent Surface Modification of Hydrophobic Polymers and Articles Made Therefrom" filed Oct. 17, 1988). A useful proportion of these groups are exposed at the membrane surface and by bringing the membrane in contact with a solution containing a linker moiety, which linker moiety is capable of forming a covalent bond with the polymer chain end group and at least one functional group of a macromolecular or ligand species, the polymer surface is rendered susceptible to modification by the subsequent introduction of said macromolecule or ligand selected for its ability to alter the surface properties of the bulk polymer. Subsequent layers of a variety of macromolecular or ligand species may then be covalently introduced by repeating the overall process although the use of the linker moiety in these additional layers is not always necessary.

A preferred linker moiety is a diepoxide, an epoxyhalide, or a dihalide and the macromolecule or ligand species may be a hydrophilic or hydrophobic synthetic or natural polymeric substance or may even be a low molecular weight compound. Biologically active proteins, polypetides, and polynucleotides may also be covalently bound to the polymer surface in like fashion.

The present invention also describes the unique characteristics of a four-component dope composition which exhibits thermal phase inversion boundaries at a so-called lower critical solution temperature (LCST) as well as at an upper critical solution temperature (UCST). These properties are exploited by a manufacturing process that employs a temperature-regulated nonsolvent quench bath which serves to initiate the temperature-dependent phase inversion phenomenon as well as freezing or precipitating out and preserving the resultant microporous structure.

In conjunction with the procedure disclosed for the production of anisotropic as well as isotropic microporous flat sheet or hollow fiber membranes, the present invention further describes an improved spinnerette assembly comprised of two independent concentric annuli surrounding a central bore which optionally contains therein a removable hollow pin. This improved spinnerette, which can be maintained at a desired temperature with the aid of means for external heating, is designed to accommodate three separate entry ports for controlling the flow of three separate fluids: namely, a dope composition, an intraannular fluid, and an extraannular fluid. The design of this improved spinnerette is quite simple and economical and has no need for tangential entry ports.

The ability to deliver the extraannular fluid over the outer surface of an extruded hollow fiber permits, among other things, the production of hollow fiber membranes with a substantially isotropic microporous structure in all directions throughout the membrane. As disclosed further below, other membrane structures (e.g., skinned, double-skinned, anisotropic) are also possible by the methods of the present invention.

4.0 BRIEF DESCRIPTION OF THE FIGURES

Figure 4:
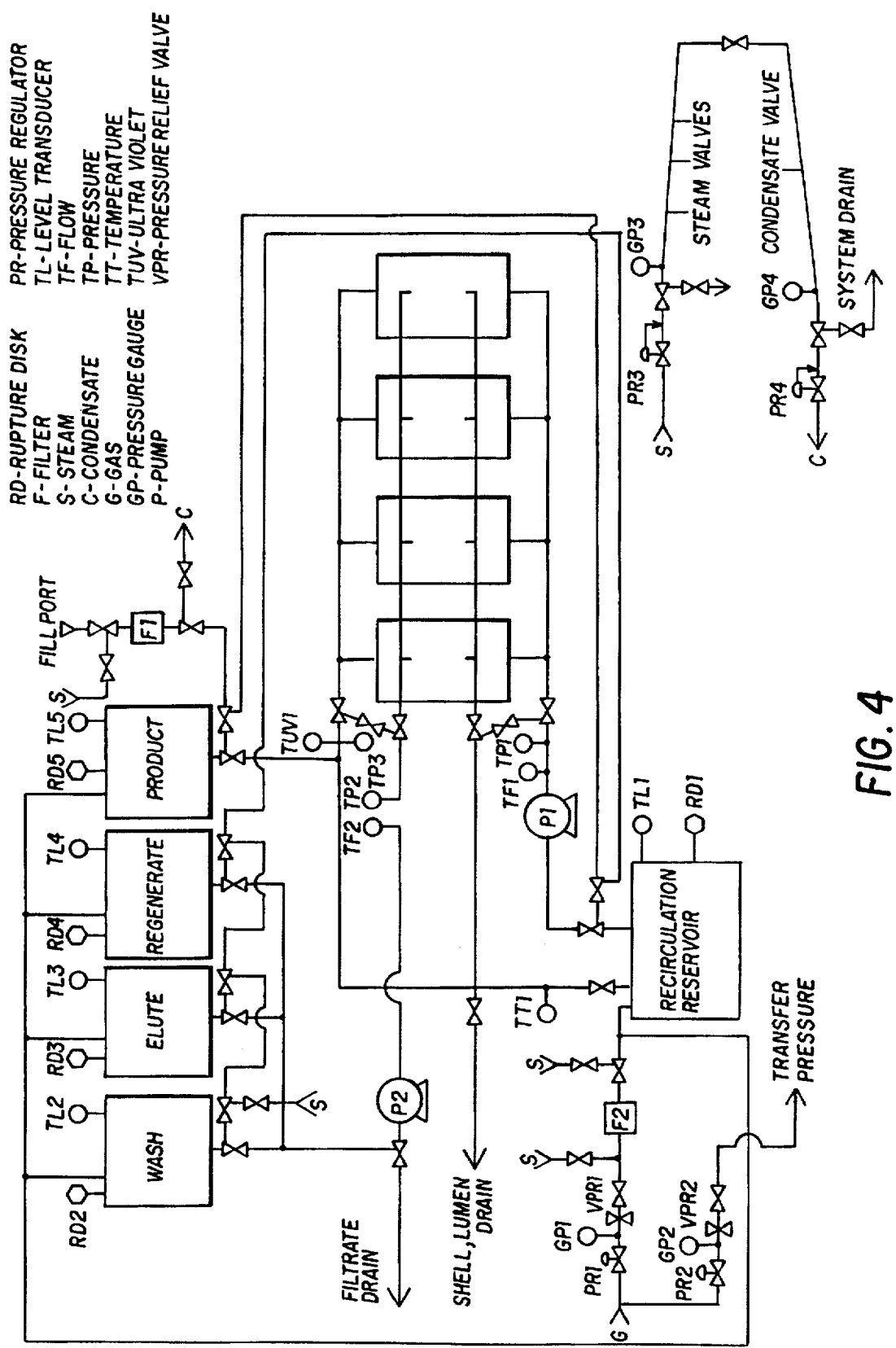

FIG. 4 large scale system operated in a sterile manner where system is under positive pressure at all times, buffers are transported into reservoirs through sterilizing filters and apparatus can be steamed in place sterilized prior to operation.

FIG. 3 illustrates membrane-mediated affinity separation steps where the membrane is in the form of a hollow-fiber membrane.

Figure 5:
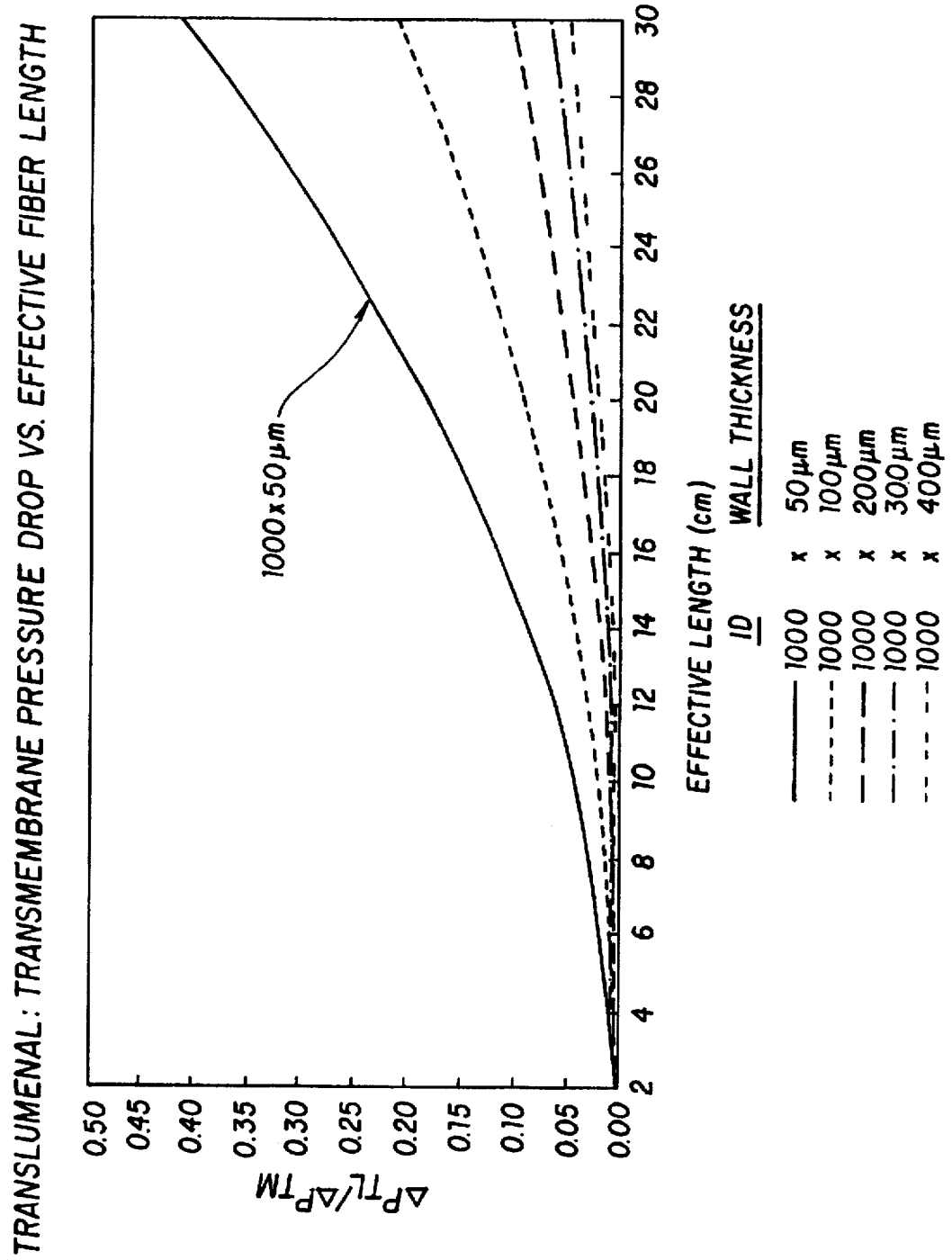

FIG. 5 illustrates calculated ratios of translumenal-to-transmembrane pressure drops as a function of effective fiber length.

Figure 6:
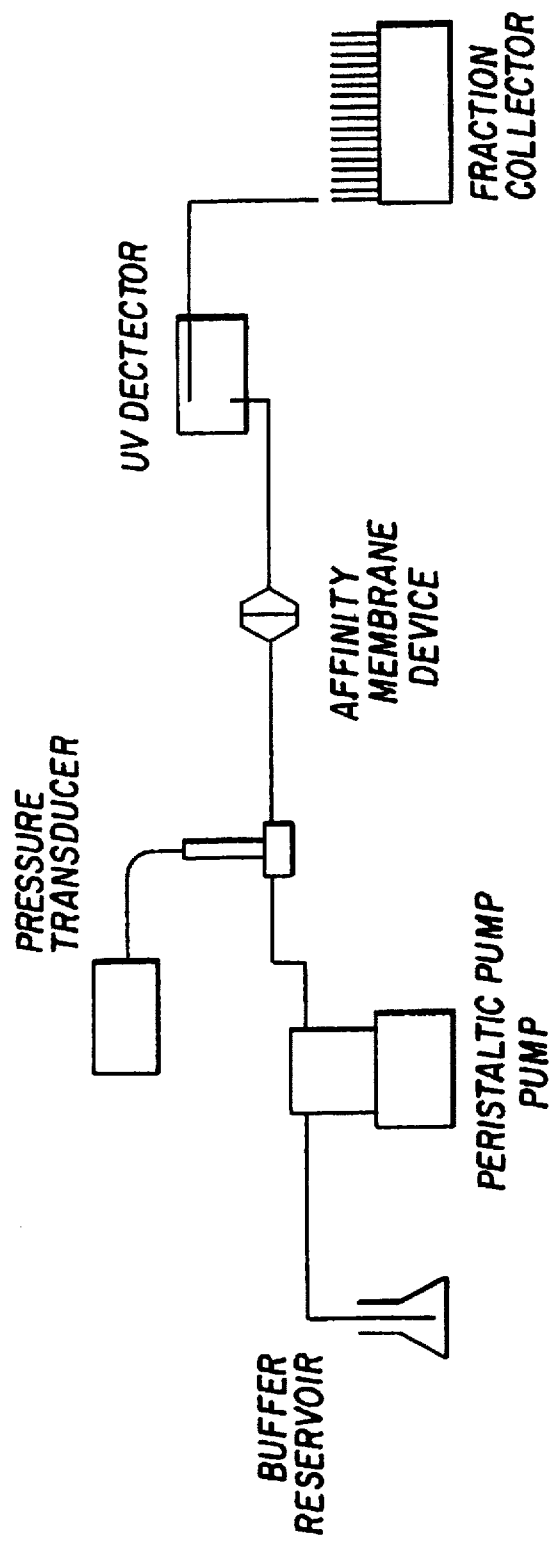

FIG. 6 illustrates an experimental apparatus used in the flat-sheet affinity membrane purification of fibronectin from blood plasma and determination of capture efficiency of human IgG from a dilute solution.

Figure 7:
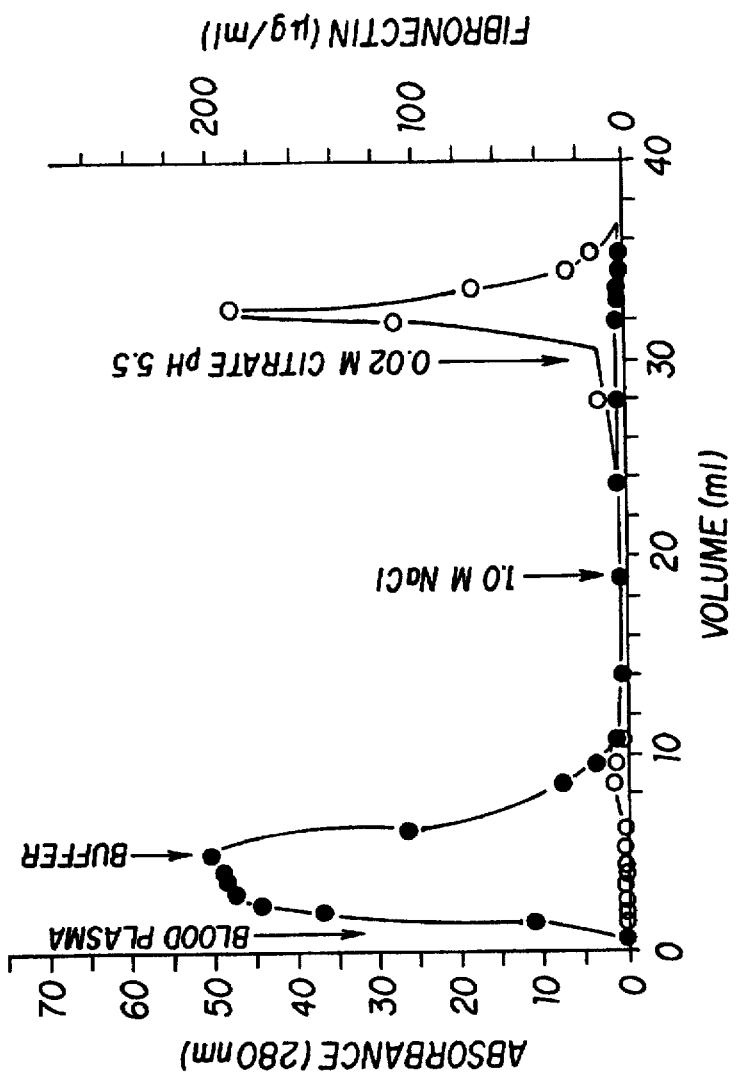

FIG. 7 illustrates results of the purification of fibronectin from blood plasma with a flat-sheet affinity membrane.

Figure 8:
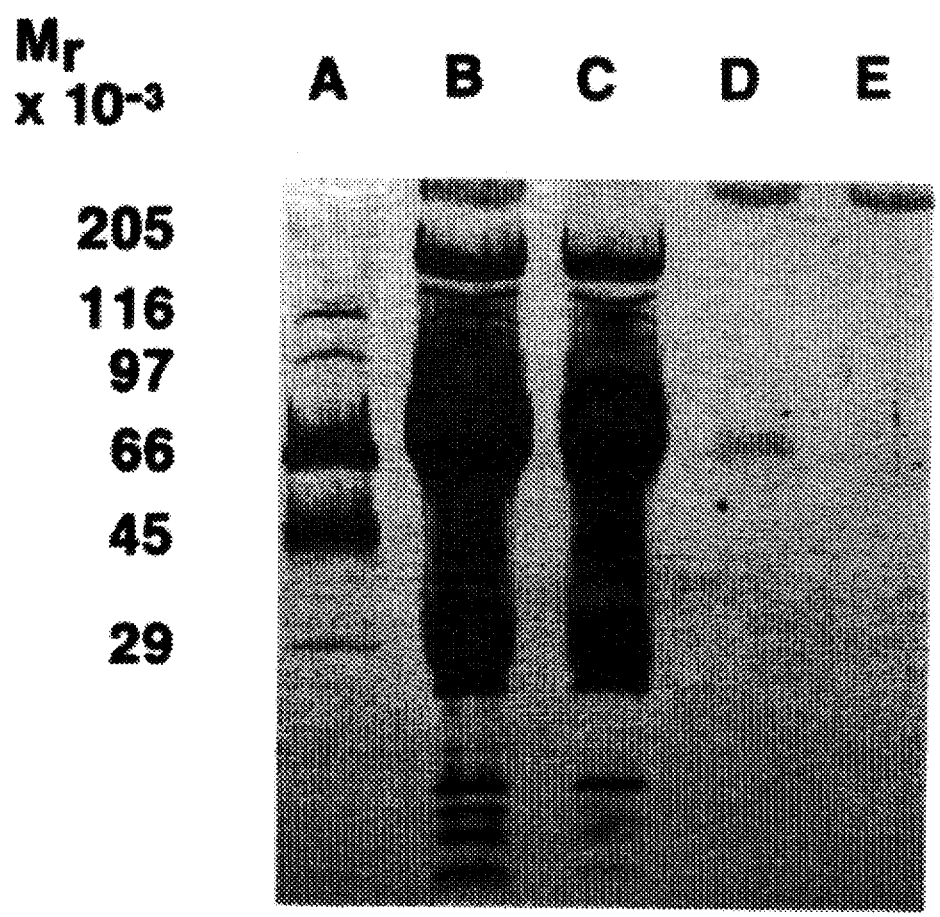

FIG. 8 shows an SDS PAGE gel used in determination of fibronectin purity and extent of depletion from affinity membrane-treated blood plasma.

Figure 9:
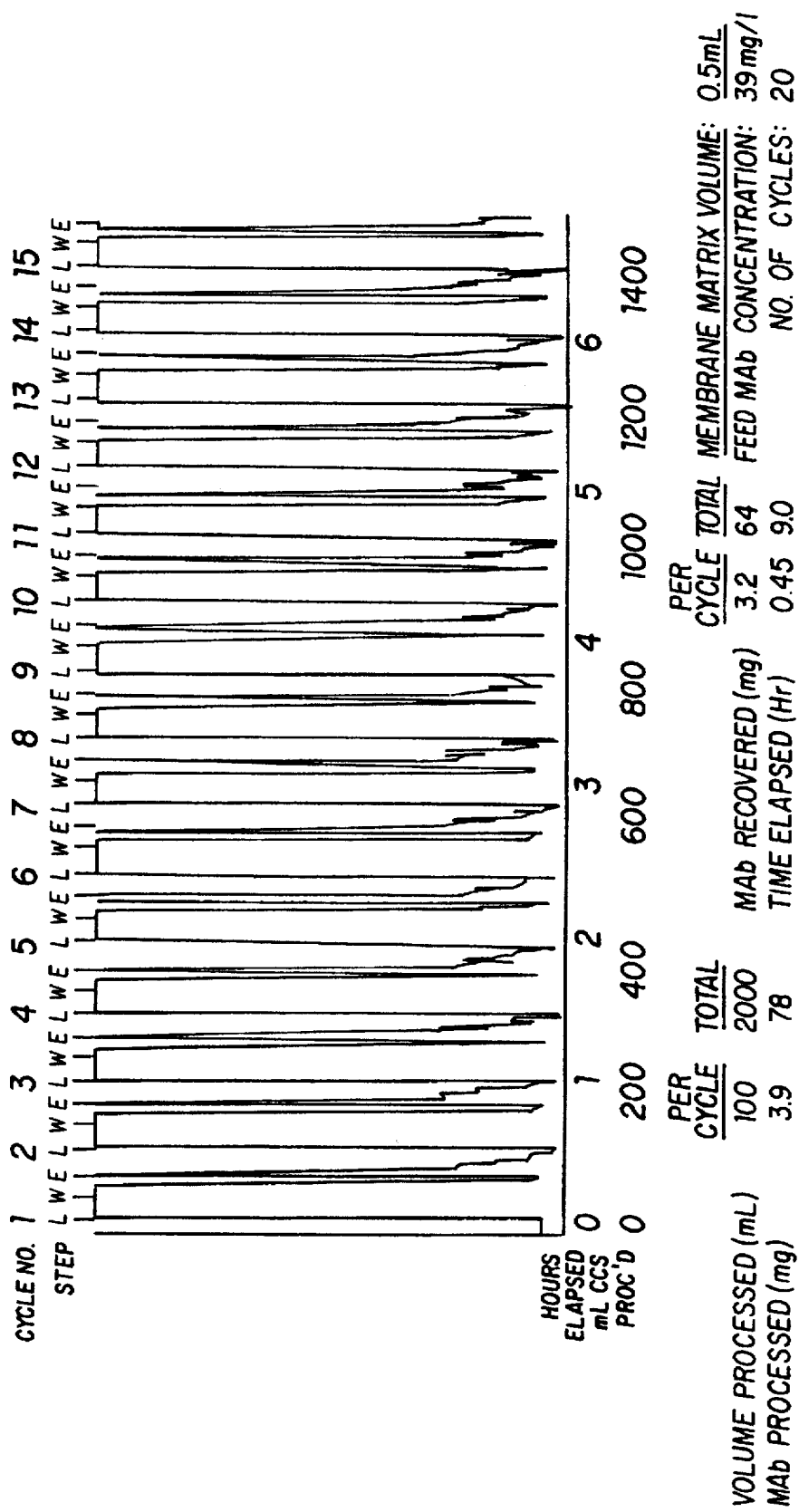

FIG. 9 shows experimental results of cycling a protein-A activated hollow-fiber affinity membrane module used in the purification of a murine monoclonal antibody from a cell culture supernatant.

Figure 10:
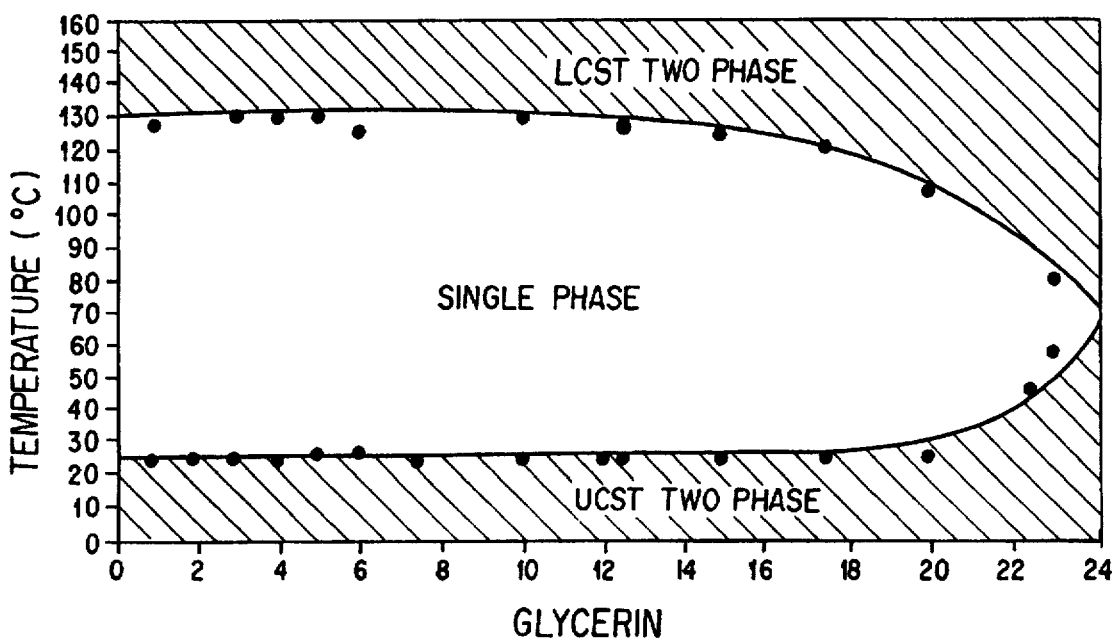

FIG. 10 Shows a phase diagram for a four-component PES/PEO dope composition.

Figure 11:
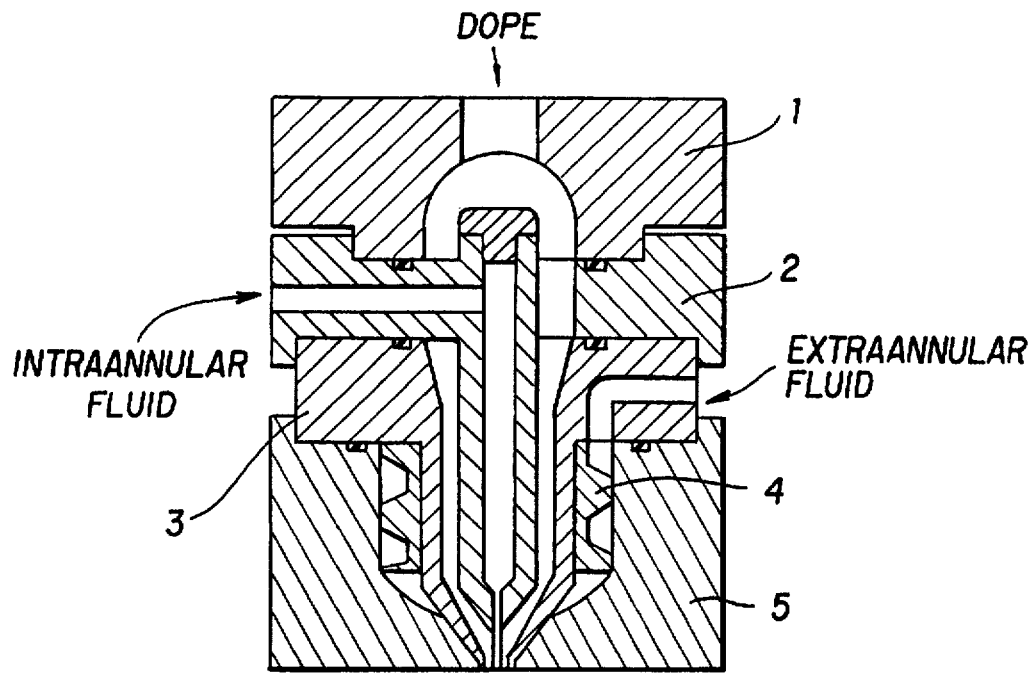

FIG. 11 Shows a schematic diagram of a spinnerette assembly.

Figure 12:
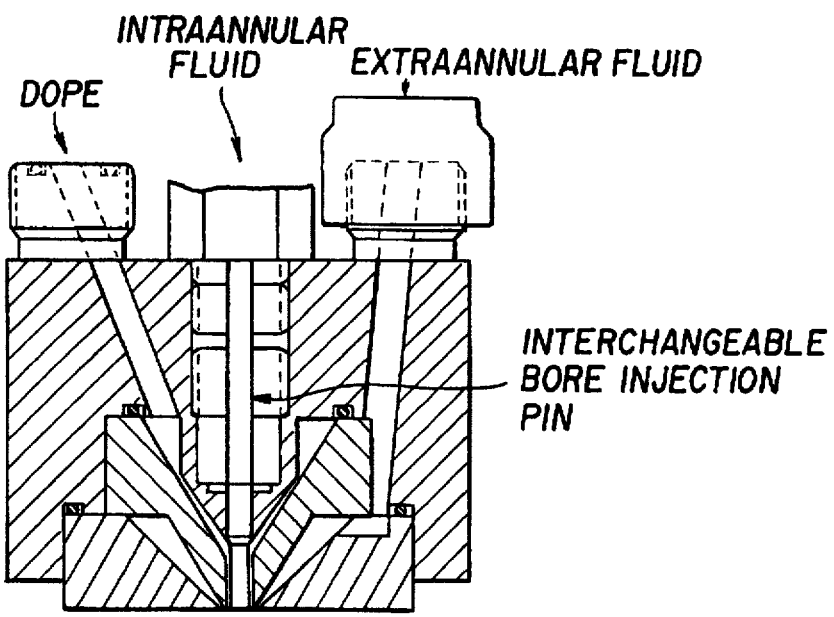

FIG. 12 Shows an alternative embodiment of the double annular co-extrusion spinnerette assembly.

Figure 13:
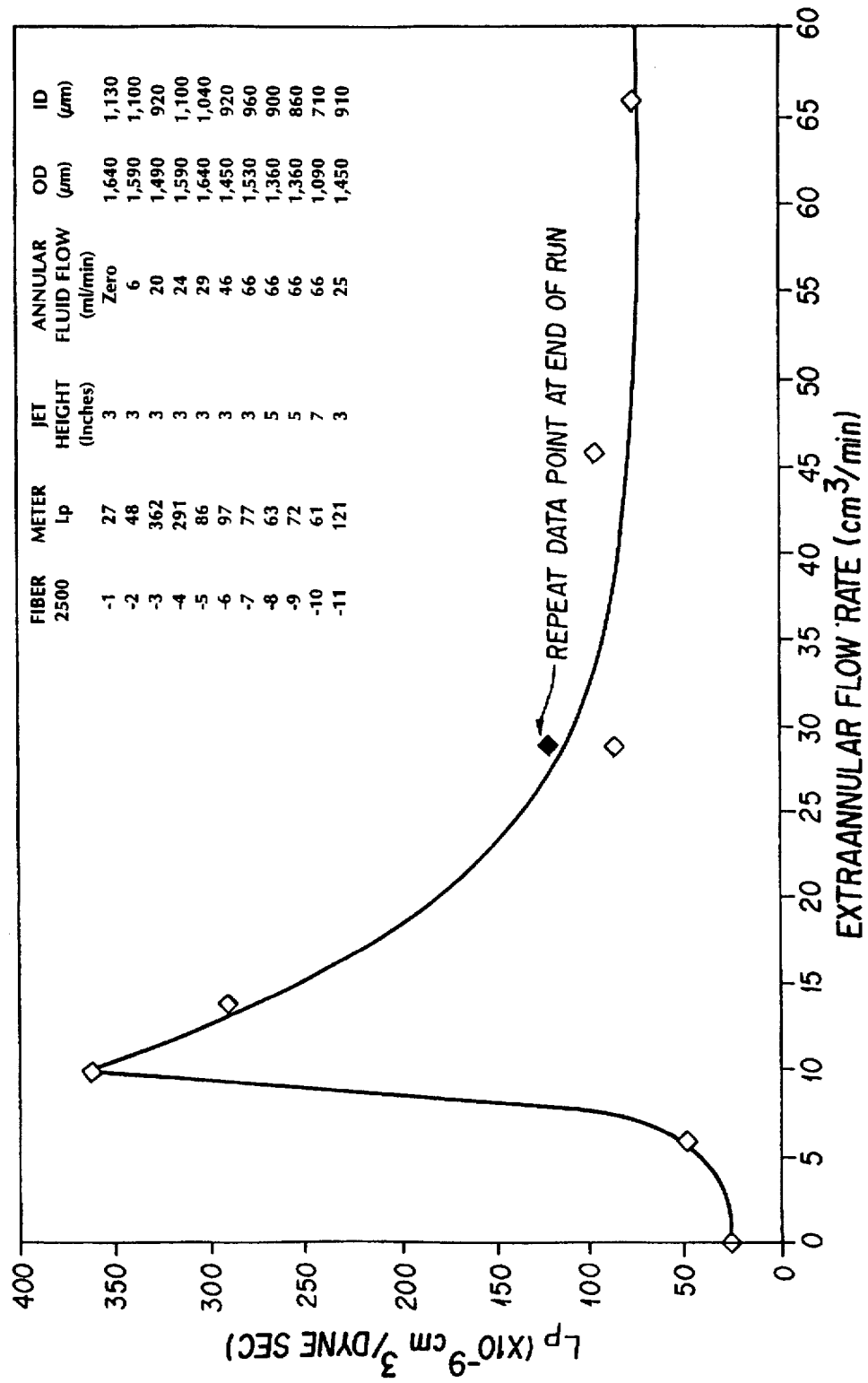

FIG. 13 Shows a plot of hydraulic permeability versus extraannular flow rate employed in fiber manufacture.

5.0 DETAILED DESCRIPTION OF THE INVENTION

5.1 General Apparatus Description

Generally stated, this invention comprises an apparatus capable of carrying out an affinity separation process for removal of target molecules from a feed stream. A ligand specific to the target molecule or ligate is anchored to a membrane in the apparatus. The apparatus capacity for the target molecule is defined by the membrane geometry, membrane characteristics and its associated ligand's binding efficiency. The apparatus preferably has separate compartments on either side of the membrane defining a feed side and filtrate side chamber. A preferred process for carrying out affinity separation in the apparatus begins by flowing a first fluid containing the target or ligate molecule through the feed chamber of the membrane device. A specified volume of the feed perfuses the membrane at a flow rate defined by the membrane device's capacity for the target molecule and regulated by the filtrate pump. The process to recover the membrane bound target molecule continues by washing the device's filtrate chamber with a buffer solution, followed by washing the membrane structure and feed chamber. Eluant is used to flush the filtrate chamber, followed by elution of the target molecule from the membrane structure, preferably into the feed chamber and out of the device. The membrane device is then equilibrated with a regeneration buffer by first flushing the filtrate chamber, and then flushing the membrane and feed chamber.

Preferably, the apparatus automatically performs the separation process with repeated rapid cycles. The apparatus membrane comprises substantially isotropic microporous membrane material on to which a ligand, specific to the target molecules, is anchored. The apparatus contains pumps and valves controlled by a microprocessor and, in its operation, is programmed to cycle through a membrane loading step with the feed stream containing the target molecule such as a protein, a washing step to remove remaining contaminants, an elution step to recover the target molecule and a membrane regeneration step to complete the cycle. Fluid containing the target molecule is recirculated with a feed pump from a reservoir and through the feed chamber of the apparatus. There, a fraction of the feed perfuses the membrane, regulated by a filtrate pump at a flow rate consistent with the device geometry and membrane characteristics, permitting the target molecule to be captured by the membrane. Eluant is used to flush the filtrate chamber, followed by elution of the target molecule from the membrane bound ligand. The membrane device is then equilibrated with a regeneration buffer by first flushing the filtrate chamber, and then flushing the membrane and feed chamber.

The ease of scale-up is again enabled by the unique membrane design. The system scales directly with membrane volume and ligand content. Operation is simplified by maximizing the automation of the process.

5.2. General Description of Affinity Membrane Process for Protein Purification An affinity membrane-mediated protein purification process takes in four basic steps (FIG. 3). In an actual hollow fiber affinity membrane device, as many as hundreds or thousands of fibers form a long cluster inside the module or container. (1) Feed solution containing the target protein is brought into contact with the immobilized affinity ligand by forcing the feed solution through the pores of the membrane. During passage of the feed through the membrane, target protein preferentially adsorbs to the bound ligand on the pore walls. Loading can be carried out in a single-pass fashion, wherein the filtrate, depleted of target protein, is discarded; or in a multiple pass format, wherein the filtrate stream is contacted with the affinity membrane more than once. The loading step can be carried out either in the cross-flow mode, wherein a portion of the the feed solution is recirculated on one side of the membrane or in a the dead-ended mode, wherein the entire feed stream is directed through the membrane wall (2) One or more wash steps to remove nonspecifically adsorbed proteins. This step can be carried out either in the forward direction (i.e., with flow in the same direction as the feed solution was convected through the walls of the membrane) or in the reverse direction (i.e., backflush). (3) An eluant is passed through the membrane, thereby effecting release of the target protein from the immobilized affinity ligand. The target protein present in the eluate is recovered, generally in purified, concentrated form. (4) A regeneration solution is employed to remove residual eluant, thereby returning the membrane to an environment conducive to binding of the target protein to the immobilized ligand in a subsequent cycle. As with the wash step, steps (3) and (4) can be conducted with fluid flow in either the forward or reverse direction.

In a preferred embodiment, the affinity membrane device is a hollow fiber module, which is configured in an automated, microprocessor-controlled system comprising feed and filtrate-side pumps and a series of valves to control the rate and direction of fluid flow. In a typical purification cycle loading is carried out in the cross-flow mode, with a recirculation rate of 30–100 device volumes per minute and a filtration rate of 1 to 20 device volumes per minute. The time required for this step is dependent on the target protein binding capacity of the device, the titer of the target protein in the feed solution and the filtration rate. Typical loading times range from one to twenty minutes.

Each wash step is typically performed in two stages, the first to flush residual filtrate from the shell side of the device and the second to wash the membrane in the direction of shell to lumen (i.e., backflush) in order to remove nonspecifically adsorbed proteins and to dislodge particulates in the lumen side of the membrane wall. Times for each wash step range from 15 seconds to five minutes and are typically 15 and 60 seconds for shell and lumen washes respectively; flow rates are typically 1–20 device volumes per minute. Wash buffers are generally sent to drain after passage through the membrane device.

Elution is performed in a fashion similar to the wash steps, i.e., in two states, except that the eluted product is directed into a product reservoir. The flow rate in the elution step is typically 1–20 device volumes per minute and the duration is typically 1–10 minutes.

Regeneration is performed in the same fashion as the wash step, i.e. in two stages—shell and lumen regeneration, with the spent regeneration buffer generally flowing to drain. Times and flow rates of the regeneration step generally fall in the same range as the wash steps.

Typical cycle times for the affinity purification process outlined above range from ten to sixty minutes.

In a further embodiment of an affinity membrane process, the affinity membrane is protein A and the target protein is a murine monoclonal antibody, which is contained in impure form in cell culture supernatant, mouse ascites fluid or a fluid derived from cell culture supernatant or ascites fluid. Loading of the protein A containing affinity device appear in the filtrate. Washing is conducted using a buffered solution at near neutral pH. Typical buffers employed for washing include PBS pH 8.0 and 1.5M glycine, 3M NaCl pH 8.9. Product elution is effected using an acidic buffered solution such as 0.1M citrate pH 3.0. Regeneration buffers are typically similar to those used for wash step.

5.3 Modified Membranes Utilized in Apparatus and Method of Their Manufacture This invention utilizes the functionalizable chain ends present in practically all polymeric materials. The instant invention provides that treatment of suitable hydrophobic polymer samples, under heterogeneous conditions, with linker moieties capable of forming a covalent bond with the hydrophobic polymer end groups, allows for the modification of the surface properties of the polymer while preserving desirable bulk properties. Using the methods of the invention, the surface properties of any article manufactured from the subject polymer may be modified while preserving the shape and microstructure of the manufactured article. Thus, bulk polymers with functionalizable end groups may be derivatized or modified under heterogeneous conditions whether the polymer is in powdered form, in the form of an extruded fiber, a microporous membrane, a solid strip, molded into a pipe, or incorporated into an artificial organ, skin, or prosthetic device. Such an article may be manufactured by techniques well-known in the art. Examples of these manufacturing methods include but are not limited to, injection, compression, and blow molding, blowing, calendering, casting, coating, forming, lamination, or extrusion methods.

Furthermore, a process for the production of substantially isotropic microporous membranes is disclosed, which process takes advantage of the special properties of a unique four-component dope composition and an improved double annular multi-port spinnerette assembly.

5.3.1 Membrane and Module Design Considerations

Development of membrane-based affinity purification device to meet the needs of downstream processing requires an integrated approach to hollow fiber development and module design.

The most important membrane and device properties to be taken into account in designing a hollow fiber affinity device are:

(i) translumenal pressure drop ($\Delta P_{TL}$) as a function of module length;

(ii) $\Delta P_{TL}$ relative to transmembrane pressure drop $\Delta P_{TM}$; and (iii) wall thickness and specific surface area in a given volume of membrane wall.

Translumenal pressure drop can clearly be minimized by producing hollow fibers with progressively larger internal diameter (ID). The following disadvantages are associated with this approach:

1. fewer fibers can be contained in a given shell volume; therefore ligand loading capacity of the device would suffer.
2. Larger shell-side volume should be employed for containment of the increased number of fibers required to maintain the predetermined ligand loading capacity, thus increasing both shell-side and lumen-side dead volumes.
3. Fibers with low wall thickness to outside diameter ratio (t/OD) are prone to physical damage (for example, fiber-collapse during backflushing), which would be the case for large ID thin-walled fibers.
4. Prior art for hollow fiber spinning technology (based on a non-solvent coagulation approach) cannot produce fibers with wall thicknesses much in excess of 100 µm without incurring severe resistances, both in the matrix and on the outer surface of the fiber.

The concept of a thick walled fiber with a large ID has important implications to module design. For example, FIG. 5 illustrates the trend in the ratio of translumenal to transmembrane pressure drop as a function of fiber length at various wall thicknesses for a fiber ID of 1,000 µm. Decrease in the $\Delta P_{TL}/\Delta P_{TM}$ ratio with increased wall thickness signifies the improvement in uniformity of transmembrane flow along the length of the module.

Another benefit of thick walled fibers is the fact that for a given total membrane volume and packing density, dead volume decreases with increasing wall thickness.

The non-linear decrease in dead volume as fiber wall thickness is increased approaches a point of diminishing returns above 300 μm (at 1,000 μm ID). The net result of this consideration in the module design exercise is a device in which shell-side volume is only a factor of two greater than lumen-side volume.

The morphology and isotropy of microporous membranes are critical to the performance of hollow fibers employed in affinity purification. Thus, pore sizes in the 0.22 um to several micron range are not expected to result in sieving of protein molecules. Membranes in this pore size range are by convention classified as microfilters (MF) based on their ability to reject particulate matter.

Any significant size distribution (i.e anisotropy, or asymmetry) within the membrane wall can cause entrapment of material and hence plugging. Because a viable affinity hollow fiber may be required to operate reproducibly for several hundred cycles in order to be—cost-effective, membrane plugging should be avoided. Furthermore, structural (and chemical) integrity of the membrane should be such that catastrophic failure does not occur during repeated cycling.

Besides reducing the likelihood of plugging, isotropy enables fluids to flow freely and unhindered in either direction across the membrane. Due to the uniform resistance, membrane of this type would present less hindrance to flow in a backflush mode of operation than a skinned membrane. Ultrafilters are always skinned and would be very short lived if employed in this manner.

As membrane pore size increases (i.e., from UF to MF type membranes), internal surface area inevitably decreases. However, microfilters have the advantage of high volumetric flux at low transmembrane pressure, and a much lower probability of fouling and/or plugging. For these reasons, a MF-type, isotropic microporous hollow fiber is a highly desirable membrane for affinity purification applications.

5.3.2 Modification Of Hydrophobic Polymer Surfaces

Almost all known polymers have at least one functionalizable end group which is originally present in the monomer precursor or is introduced via the polymerization process. Thus, poly(ethylene oxide) has terminal hydroxyl groups, polyethersulfones have a halide at one end and a substituted phenol at the other, polyimides have terminal carboxyl and amino groups, and polyesters have terminal carboxyl and hydroxyl groups, to name a few polymers. Moreover, polymers prepared by free radical polymerization contain a functionalized initiator fragment at some of the polymer chain ends. For example, a vinyl halide, polymerized in the presence of azobis(isobutyronitrile), would contain a tertiary nitrile group in some of the chain ends. The proportion of polymer chains bearing the initiator fragment may be adjusted by varying the composition of the starting monomer/initiator mixture or the polymerization conditions.

The present invention is directed to the functionalizable groups inherently present at the polymer chain ends. Furthermore, the present invention finds its most significant utility in derivatizing hydrophobic engineering homopolymers, copolymers, or blends having relatively inert monomer units in the polymer backbone. These types of polymers are generally prepared by step, radical chain, ionic chain, ring opening, or Ziegler-Natta polymerization and are generally regarded as being completely inert and not amenable to derivatization or modification by the mild conditions disclosed in this invention. Examples of these polymers include, but are not limited to polysulfones, polyethersulfones, polyimides, poly(arylene oxide), polyarylene sulfide, polyquinoxaline, polysilane, polysiloxane, polyurethanes, poly(etheretherketones), polycarbonates, polyesters, poly(vinyl halides), and poly(vinylidene polyhalides), derivatives, blends, mixtures, or copolymers thereof.

Further, although only one functionalizable end group need be present in a polymer chain, the number of available groups may be increased by chemically converting inherently less reactive or less useful end groups to more useful functionalities. For instance, terminal nitrile groups, introduced by the free radical polymerization using nitrile-containing initiators, may be reduced to amines using any of a wide variety of reducing agents available to the practitioner. Metal hydride reagents can serve this purpose, for example. Aromatic halide groups of polyarylsulfones can be converted to aryloxy groups by treatment with aqueous base. Also, isocyanate groups of polyurethanes may be converted to amines. In this manner, the number of useful terminal groups may be increased without affecting the integrity of the polymer backbone.

In addition, it has also been discovered that preconditioning polymer samples or articles manufactured therefrom by washing or heating the samples in aqueous or nonsolubilizing organic solvents increases the efficiency of the subsequent derivatization steps. Not seeking to be limited by theory, it is believed that the polymer interface or the surface of the manufactured article may be contaminated with foreign materials or processing aids thus shielding the functionalizable end groups. Washing the polymer samples may simply provide a means for mechanically stripping away these contaminants and exposing more of the polymer chain ends present at the surface or interfacial boundaries. Preferred organic solvents include, but are not limited to, acetonitrile and isopropanol. Aqueous solutions of these solvents may also be used.

In one preferred embodiment of the invention, flat sheet microporous membranes, comprising polyethersulfone (PES) as the primary or bulk polymer component, are immersed overnight at room temperature in a basic aqueous solution containing a diepoxide linker moiety. Optionally, the membrane samples may be preconditioned by heating them in aqueous solutions or washing them in acetonitrile or isopropanol. The substituted phenol groups of the PES chain ends exposed at the membrane surface are deprotonated by the base giving a nucleophilic phenoxide group. This nucleophile attacks an epoxide group of the linker moiety forming a covalently bound (i.e., ether bond) linker moiety. Because the covalently bound linker moieties are capable of forming at least one other covalent bond (via e.g., a second epoxide group) with another chemical entity, any molecule, macromolecule, or ligand, may then be covalently bound to the membrane surface. The covalently bound macromolecule is thus held very strongly and cannot be removed by washing or other mechanical means.

It is understood that the linker moiety serves to covalently bridge available functionalizable polymer chain ends with functional groups present on the macromolecule of choice. Thus the linking agent may preferably take the form of any polyfunctional organic molecule such as aliphatic or aromatic compounds bearing epoxide, carbonyl, carboxyl, amino, halo, hydroxyl, sulfonyl halides, acyl halides, isocyanate or combinations of these or other functional groups so long as the linker moiety is stable, compatible, and able to form covalent bonds with the bulk polymer and macromolecular or ligand species. The linker moiety may even incorporate inorganic functionality such as silicon, boron, aluminum, tin, phosphorous, sulfur, or nitrogen groups. It is within the scope of the present invention that other variations incorporating silicates, aluminates, borates, stannates, phosphates, or sulfonates, for instance, may also be used as the primary bridging group. However, ethylene glycol diglycidyl ether (EGDGE), 1,4-butanediol diglycidyl ether, epichlorohydrin, aliphatic dihalides, diacids, diacid halides, disulfonyl halides, and triazines are preferred embodiments of the linker moiety.

Figure 1:
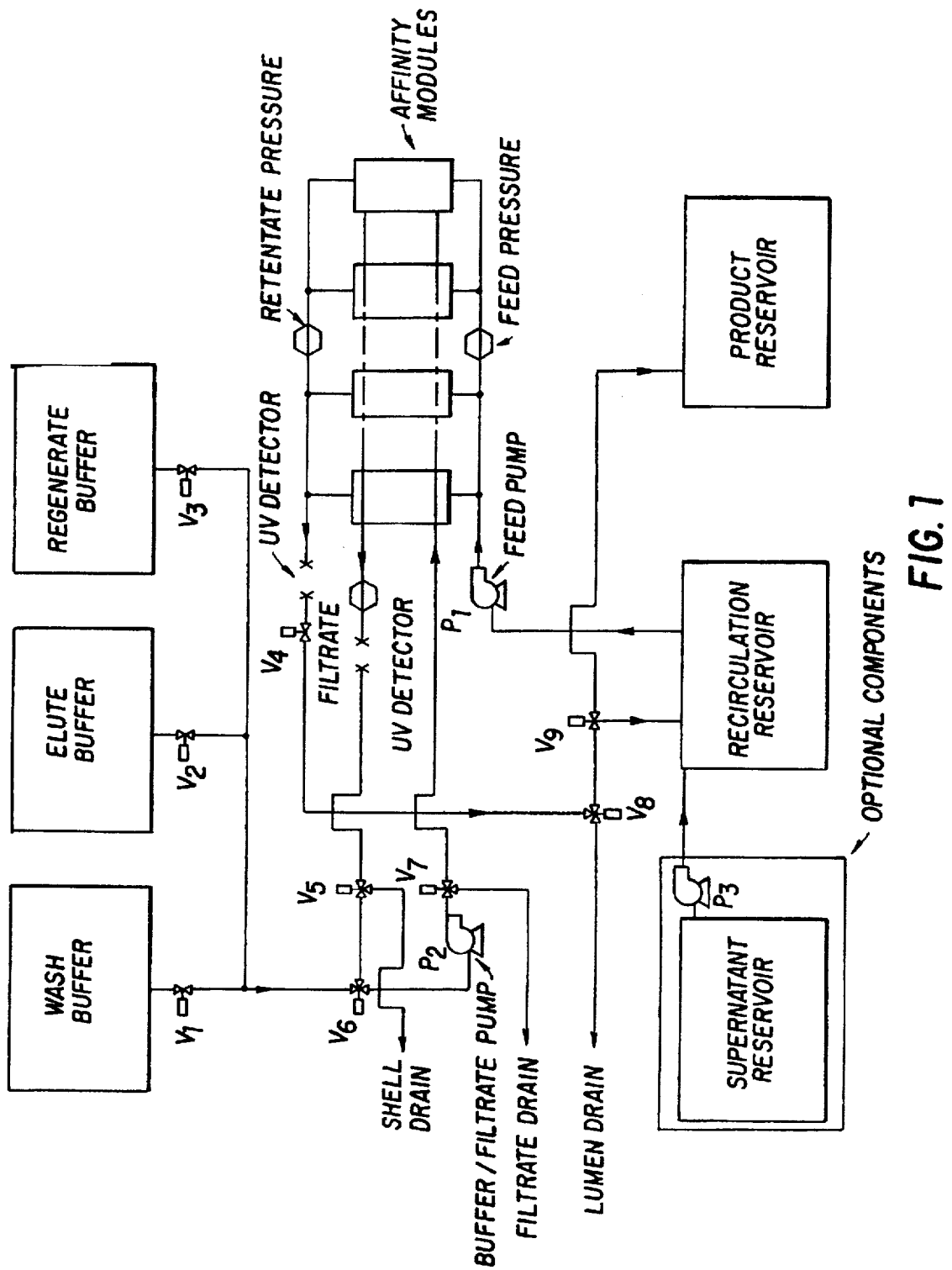
FIG. 1 illustrates the preferred small-scale membrane affinity apparatus operated in a non sterile matter including pump means, valve means, piping means and solutions along with indications of material flow directions through the apparatus.

As mentioned above, the macromolecular or ligand species selected to modify the membrane surface or, more generally, any hydrophobic polymer surface, should preferably be capable of altering the surface properties of the hydrophobic polymer, membrane, or manufactured article and have at least one functional group which is able to form a covalent bond with the linker moiety. In some cases, one type of functionality may suffice. For example, the —OH groups of hydroxyethylcellulose (HEC) convey hydrophilicity to the hydrophobic membrane surface and also form ether bonds with the pendant epoxide groups of the covalently bound EGDGE. Depending upon the end use applications, therefore, the macromolecule can be comprised of molecules of low molecular weight, oligomers of intermediate molecular weight, or polymeric substances of high molecular weight. Preferably, the macromolecule is of high molecular weight and may include, but is not limited to, surfactants, carbohydrates, lectins, polypeptides, polysaccharides, liposomes, proteins, glycoproteins, oligonucleotides, synthetic dyes, natural dyes, polynucleotides, derivatives, or mixtures thereof. Molecules or polymers which are capable of bearing a charge, either cationic or anionic, or those bearing nonionizable groups are also useful. FIG. 1 (of copending application of Azad and Goffe entitled "Process for the Covalent Surface Modification of Hydrophobic Polymers and Articles Made Therefrom" filed Oct. 17, 1988), is a schematic depiction of part of the basic processes of the invention.

Preferred macromolecular species include polysilanes, polysiloxanes, hydroxyalkylcellulose, dextran, carboxymethylcellulose, poly(ethylene imine), poly(carboxymethylethylene imine), poly(vinyl alcohol), derivatives, blends, mixtures or copolymers thereof. The macromolecules may also be biologically important molecules and may include, but are not limited to monoclonal antibodies, polyclonal antibodies, antigenic substances, enzymes, carrier proteins, coagulation factors, cofactors, inhibitors, hormones, immunoglobulins, histones, plasmids, derivatives, or mixtures thereof.

It should be apparent that the process for covalently binding the macromolecule to the polymer chain ends can be repeated several times. Subsequent applications are likely to utilize functionalizable groups of the first macromolecular layer, however, because these groups are present in much greater concentrations than the remaining unutilized polymer chain ends. Each successive binding thus involves increasing numbers of linker moieties resulting in a stronger bond as well as greater amounts of loading on the membrane surface. For this reason, it may sometimes be more advantageous to "amplify" the surface functionalizable groups present on a membrane surface by first applying one or more layers of a readily available macromolecular species before applying a more valuable ligand species on the top layer. In a case where layers of hydrophilic macromolecules are covalently attached, the nonspecific protein binding of the modified surface is lowered dramatically versus the virgin hydrophobic surface.

The covalent binding of the surface ligand layers need not necessarily involve the intermediacy of a linker moiety although in certain cases, a "linker molecule" is best employed. It is possible, for example, to render certain functional groups of macromolecules already bound to the polymer surface more reactive towards the functional groups of an added ligand by employing activating reagents. These methods which lead to active sites on the macromolecule are well known in the art and include the use of such reagents as dialkylcarbodiimides (for forming amide bonds), diazotization (for coupling aromatic groups), cyanogen bromide (most commonly used for the activation of solid supports), epoxides, sulfonyl chlorides, or other processes, such as the use of 2-fluoro-1-methylpyridinium p-toluensulfonate (FMP), which facilitate the coupling reaction by introducing a superior leaving group. Other nonlimiting reagents which may be used to covalently bind the ligand to the macromolecule or polymer surface include diepoxides, haloepoxides, 2,4,6-trichloro-S-triazines, diacid chlorides, dialdehydes, diisocyanates, or haloalkylcarboxylic acids.

In a specific preferred embodiment of the invention, Protein A molecules may be bound directly by using EGDGE as the linker moiety to the polymer chain ends of a hydrophobic PES membrane. Preferably, the PES membrane is first modified by applying a few layers of hydroxyethylcellulose. Other hydroxyl-containing macromolecules such as dextran, agarose, hydroxypropylcellulose, or poly (vinyl alcohol) may be used with equal efficacy. After the number of hydroxyl groups on the membrane surface is thus "amplified," the membrane is treated with FMP to generate active sites on the membrane surface. The membranes are then exposed to a slightly basic buffered solution of Protein A to effect efficient covalent attachment of this valuable ligand.

Membrane samples with covalently attached Protein A are quite useful, for instance, in the selective binding and isolation of human immunoglobulin G (IgG) from a mixture of serum proteins. This utility is demonstrated in the Examples section of this specification.

It is evident that many types of ligands can be bound to the hydrophobic membrane by the methods of this invention. Natural products and biologically active components as well as synthetic polymeric materials may be used. All the types of molecules listed above as possible macromolecular species, for example, may also comprise the ligand species. Additional non-limiting examples include dyes, enzyme inhibitors, amphoteric, ionizable molecules, hydrophobic long chain aliphatic hydrocarbons, aromatic hydrocarbons, and the like. Silane derivatives may also be useful, not only as simple ligands, but as potential polymerizable species. Examples of these silanes include but are not limited to terminal amino aliphatic hydrocarbon trialkyloxy silanes, such as aminoethyl aminopropyl trimethoxysilane, carboxyl-substituted silanes, long chain aliphatic or aromatic hydrocarbon silanes, and the like. Many types of functional groups may, of course, be present in the silane compounds.

Preferred ligands include natural or recombinant Protein A, Avidin, Biotin, Heparin, animal, plant, bacterial cell surface receptors, antibodies against IgG, IgM, IgA, IgE, tissue plasminogen activator (TPA), human interleukin (IL) proteins, human chorionic gonadotropin (HCG), thyrotropic hormone (TSH), carcinoembryonic antigen (CEA), α-fetoprotein, transforming growth factor (TGF), interferons, and blood coagulation factors such as Factor VIII or IX. In general, ligands capable of binding specific ligates from a sample solution or mixture with a dissociation constant of about $10^{-2}$–$10^{-12}$M are preferred. Those with binding constants less than about $10^{-6}$M are highly preferred. Other preferred ligands and possible substrates or ligates are listed in U.S. Pat. No. 4,693,985. The entire disclosure of this reference is incorporated herein by reference.

Still other examples of useful ligands may be easily found in catalogs for products useful in molecular biology research (See, e.g., ligand index in the Pharmacia Affinity and Chromatography Media catalog incorporated, herein by reference). An abbreviated list is illustrative: acetylglucosamine, anti-A lectin, arginine, butylamine, castor bean lectin, Cibacron Blue, coenzyme A, decylamine, diadenosine pentaphosphate, gelatin, hemoglobin, iminodiacetic acid, HMG-CoA, lysine, NADP, oligo(dA, dC, dG, dI, or dT), PHA-L, polyriboguanylic acid, poly(I)poly(C), Procion Red, uridine nucleotides, or conjugates thereof. The only limitation on the ligand species is that it have at least one functional group with which to form a covalent bond with the linker moiety or the active sites on the macromolecule.

In addition, potentially any article manufactured from a polymer which has functionalizable chain ends may be modified by the process of the invention. In particular, plastic components of artificial organs, tissues, or prosthetic groups may be made into any shape, taking full advantage of the processability and strength of the engineering polymer. These materials may then be made more biocompatible by modifying their surface properties by the process described herein. Of course, the general areas of purification, separation, filtration and, in particular membrane technology are significantly advanced by the present methods.

5.3.3 Process For Manufacturing Substantially Isotropic Microporous Membranes

The process for derivatizing hydrophobic polymer interfaces discussed above is especially applicable to the surface modification of microporous membranes. In the course of devising new ways of preparing membranes, the inventors have discovered a unique four-component dope composition which in combination with other aspects of the overall manufacturing process provides membranes with substantially isotropic microporous structures formed either as flat sheets or, perhaps more significantly, hollow fibers.

5.3.3.1 Dope Composition

This novel dope composition comprises a primary polymer component, a secondary polymer component and two solvents, the first of which is an effective solvent for both polymers (i.e., one in which both polymers readily dissolve), and the second an effective solvent for the secondary polymer component but a nonsolvent for the primary polymer component (i.e., one in which the primary polymer is poorly or sparingly soluble, or, preferably, substantially insoluble). It is the latter solvent component which conveys a certain degree of incompatibility or instability to the resulting dope mixture, and by judiciously adjusting the relative amounts of the various components, the critical parameters, such as the lower and upper critical solution temperatures (LCST and UCST, respectively) which characterize the dope composition, may be optimized to better fit the desired processing steps.

An important feature of this invention is selection of the polymer pair to be employed in the dope. Relatively good compatibility is needed to enable the manipulation of the phase boundary as a function of the nonsolvent content (e.g., glycerin) to the extent desired. Compatibility can be defined very generally in the following way: when two polymers can be co-dissolved in a common solvent (or mixture of solvents) in any ratio at 5–50% total solids to obtain an optically clear solution at a manageable temperature, such a solution is said to be compatible.

As in the case of the PES/PEO (primary/secondary polymer components, respectively) polymer pair, a solvent such as glycerin serves both as a solvent for one polymer while acting as a nonsolvent for the other. The polymer for which this liquid is an effective nonsolvent comprises the major or primary component of the final membrane desired (in this case, PES). The polymer which is soluble in both solvents should also possess hydrophilic character, such as water-soluble polymers, but is not limited to this group. However, one should keep in mind that when a water-soluble polymer is used, higher molecular weight forms are statistically more likely to be retained in the final membrane by chain entanglement than those of lower molecular weight when an aqueous quench is employed in manufacture. This entrapment, in itself, may be desirable because a certain degree of hydrophilicity and wettability is imparted to the otherwise hydrophobic membrane surface.

A broad range of hydrophilic polymer (e.g., PEO) molecular weights are useful in this invention, from molecular weights in the tens of thousands (e.g., PEG) up to millions in molecular weight). The preferred molecular weight for PEO is no less than 100,000.

An important advantage of the PES, polysulfone (PS), and other high glass transition/melt temperature polymers as the main component in these blends, is that their use results in membranes which can be autoclaved repeatedly without detrimentally altering membrane properties. Indeed, autoclaving can, in fact, increase tensile strength of PES/PEO fibers, presumably by enabling polymer relaxation to occur and thereby prevent the slow tightening or densification process observed with solution cast membranes over days, weeks, or even months. Such a densification process often leads to a reduced hydraulic permeability over time. Finally, PES/PEO fibers are sufficiently hydrophilic (by virtue of the presence of some PEO at the surfaces of the membrane) that wet/dry cycling can be done without wetting aids and with no change in performance.

Examples of other suitable polymer pairs which may be utilized in this invention include, but are not limited to: polysulfone (PS)/PEO; PES/Polyvinyl pyrrolidone (PVP) (particularly the high molecular weight forms, e.g., MW about 360,000 of PVP); PS/PVP (MW ~360,000); Polyvinylidene fluoride (PVDF/PEO; PES/Epichlorohydrin copolymers of PEO; PES/Polyvinyl alcohol (PVA); Polyphenylene oxide (PPO)/Hydrophilized forms of polystyrene (including copolymers and sulfonylated polystyrene); poly(acrylonitrile) (PAN) and copolymers/ hydrophilic acrylic polymers (including polyacrylamide), or PVP; PES/hydrophilized forms of PES (including sulfonated PES); and PS/hydrophilized forms of PS.

Suitable solvent/non-solvent pairs are numerous but are preferably within the definition of compatibility and selection of the polymer pair stated previously. Generally speaking, the class of heterocyclic or amine-containing solvents (including dimethylformamide, N-methyl pyrrolidone, dimethylacetamide, and piperidine) and polar aprotic solvents such as dimethyl sulfoxide and the like are excellent and preferred choices as first solvents for both polymers by virtue of their relatively high boiling points, polar character and water miscibility. Alternatives to glycerin as second solvents with both solvent power for the secondary polymer component and nonsolvent power for the major polymer component include: 2-methoxyethanol, formamide, ethylene glycol, various alcohols and the like.

For ease of processing it is preferred to use aqueous quench/wash baths, but this process need not be so limited. Similarly, the allowable ranges for the LCST and UCST phase boundaries are limited only by attainable temperature ranges based on available equipment and suitable quench media. In a process based on an aqueous quench/wash, the preferred ranges for phase boundaries are: LCST about 80° C. and UCST about 50° C.

In a preferred embodiment of the invention, polyethersulfone (PES), a hydrophobic polymer, is selected as the primary polymer component of the dope composition. Poly(ethylene oxide) (PEO), N-methylpyrrolidone (NMP), and glycerin make up the secondary polymer component, first, and second solvents, respectively. The cloud point phase diagram for a series of dopes comprised of 20 wt % PES and a mixture containing 7.5 wt % PEO in NMP containing varying amounts of glycerin, as a percent weight of the total mixture, is shown in FIG. 10. As shown the range of temperatures in which a single phase homogeneous composition is obtained, can be varied for a given PES/PEO ratio depending on the amount of nonsolvent present. Thus the single phase temperature range can be as wide as 100° C. to as narrow as a few degrees. In most cases, the preferred range is about 30°–40° C. For the four component dope composition, it has surprisingly been discovered that a temperature phase inversion occurs not only at temperatures below the UCST but also at high temperatures, above the LCST (See FIG. 10).

5.3.3.2 Flat Sheet Membranes

It has also been discovered that membranes with substantially isotropic porous structures (i.e., structures in which the pore diameters are within about an order of magnitude or so of each other) can be prepared and preserved by subjecting the homogeneous dope composition to an abrupt change in temperature, preferably at or above the LCST, and essentially simultaneously "freezing out" the precipitated structure by introducing a nonsolvent for at least the primary polymer component. This procedure is most conveniently carried out in the case of flat sheet membranes, by immersing a liquid film of the dope composition in a nonsolvent quenching bath (e.g., water) maintained at a temperature above the LCST. Quenching the mixture above the LCST produces more open membrane structures with larger isotropic pores in the micron range. By contrast, anisotropic microporous or macrovoid-containing membranes are obtained from quench baths held below the LCST or UCST. The membrane pore sizes, besides being substantially isotropic, may thus be potentially controlled by selecting the temperature of the quench bath. Furthermore, the membranes produced by quenching above the LCST are substantially skinless having a very high density of pores in the exterior surface of the membrane.

In effect this invention has succeeded in harnessing a thermal phase inversion process initiated at a high temperature by an almost instantaneous change in the temperature of the entire dope composition which, in turn, is brought about by immersing the solution in a quenching bath. Not seeking to be limited by theory, it is believed that the resulting microphase separated binary polymer system has a substantially isotropic microstructure as a result of the uniform rapid transfer of heat. The microstructure is then "frozen" and preserved in the integral membrane by a secondary process, occurring simultaneously with the thermal phase inversion, involving the diffusion of the nonsolvent quenching medium. This combination of a high-temperature phase inversion and nonsolvent quench processes provides membranes which are substantially isotropic and which can be made relatively thick and self-supporting. The description substantially isotropic is meant to encompass perfectly isotropic pore size distributions as well as a distribution of pore size within about one order of magnitude as determined by porometry, by passage of latex spheres, or by examination using scanning electron microscopy (SEM). Methods for determination of particle size by porometry are documented in the "Operator's Handbook for Coulter Porometer", issue A, June 1986, Part 9903175 (issued by Coulter Electronics Limited, Northwell Dr., Luton, Beds., England).

While current techniques for preparing microporous hollow fibers are capable of producing membranes with surface pores ranging from tenths of a micron to several microns in diameter, such conventional membranes of the prior art typically retain particles more than an order of magnitude smaller than the surface pore size. As an example, the nominal 0.2 μm-rated hollow fiber commercially available from AG Technology (Needham, Mass.) has been found to substantially completely reject latex spheres as small as 0.03 μm; which is more than an order of magnitude smaller than the surface pore size of about 1 μm as revealed by SEM examination. Furthermore, SEM examination reveals that pores rapidly decrease in diameter to less than 0.1 μm below the lumen surface over a distance of a few microns. SEM studies of such a membrane after a 0.03 μm latex challenge test shows entrapment of latex particles within the finely porous region in the matrix below the lumen surface.

A typical microporous hollow fiber of the present invention was determined by SEM to contain surface pores in the range of 1 μm. Latex sphere challenge tests, as a means for defining isotropy, show that latex particles as large as 0.25 μm passed freely across the membrane wall. Furthermore, SEM examination of the hollow fiber wall confirmed that pore size distribution across the entire membrane wall was substantially isotropic, with the smallest pores in the fiber wall typically being no smaller than about 0.3 μm.

It has surprisingly been discovered that a reverse pore-size distribution (i.e., large pores near membrane/solvent interface and smaller pores within membrane matrix) membrane can be prepared by a modified quench bath which contains in it a sufficient amount of strong solvent to swell the pores of the portion of the membrane in contact with the bath. After the desired pore sizes have been achieved, the strong solvent is diluted and eventually displaced with a nonsolvent wash composition. The resulting membranes can be made relatively thick and self-supporting in this fashion using the four-component dope described above. These membranes are useful in a variety of microfiltration applications particularly in the separation of blood cells from whole blood.

By employing the manufacturing process disclosed in the present invention, substantially isotropic self-supporting membrane structures of high solid content can be made. It is believed that initiating the phase inversion process at higher temperatures results in a less viscous system in which greater numbers of polymer component molecules migrate to their respective domains before the solidification or precipitation of the membrane. Such a migration process could be responsible for the larger pore structures observed for membranes prepared from quench baths kept above the LCST.

5.3.3.3 Improved Co-Extrusion Spinnerette And Production of Hollow Fibers

For the production of hollow fiber membranes having substantially isotropic microporous structures, manufacturing procedures more sophisticated than immersing a liquid film of dope composition into a quenching bath (i.e., in the production of flat sheets) are required. For this purpose an improved spinnerette assembly a schematic diagram of which is shown in FIG. 4, is used.

The "co-extrusion" spinnerette assembly depicted in the figure is part of an overall manufacturing system which includes among other things, pots for mixing, stirring, and holding the dope composition; pipes, tubing or feed lines to introduce and deliver reagents, solvents, dopes, or fluids; pumps; stirrers; baths; and heating units to control the temperature of these devices, including the spinnerette assembly. An important feature of the present spinnerette is that no more than three fluid entrance ports are necessary to achieve the desired flow distribution within the device. That is, there is one port for each of the flow paths. The flow of each fluid through each port can be independently manipulated providing greater flexibility and simplicity to the overall process control. Moreover, the flow rate of the respective fluids can affect the structural characteristics of the resulting fiber.

The co-extrusion spinnerette of FIG. 4 embodies the central feature of this invention, while providing a wide degree of versatility in the use thereof (consistent with the above teachings). As alluded to above, there are three fluid paths formed by four or five modular parts. These parts are listed below in the order in which they are labeled in FIG. 11.

1. The top portion provides containment of the dope at the top of the device and an entrance port for said dope;
2. This portion consists of a ring with a plurality of spokes radiating to the center where the spokes provide support for the hollow bore injection pin—the bore or intraannular fluid for making a hollow fiber passes through one of these spokes to the bore injection pin;
3. The port for the extraannular fluid is contained in this portion, and in conjunction with portion 5, the extraannular space is formed;
4. An optional spiral device is provided, which is designed to overcome any flow distribution problems which may arise from high viscosity solutions entering the extraannular space from a single port;
5. The face-plate of the spinnerette contains the surface (pointing downward towards the quench bath), on which the double annular configuration of this invention is evident.

Numerous alternative embodiments of this invention are possible. One example is depicted in FIG. 12, where the central theme of two mutually concentric annuli configured around a hollow pin is maintained. In this case the design emphasizes ease of device manufacture, where mass production of identical spinnerettes can be accomplished most effectively. Furthermore, by making the bore injection or intraannular fluid pass through the device vertically, it enables the use of interchangeable pins. This feature provides additional cost savings as damaged pins can be replaced modularly. Also, fibers of different dimensions can be produced readily by changing pins and/or modifying the face-plate portion.

Using the present device, an intraannular or bore injection fluid, which may be a gas, a vapor, or a liquid, can be made to emerge from the hollow pin of the central bore. Examples of a preferred intraannular fluid include, but are not limited to, an inert gas, water, water vapor, a water-miscible organic solvent, an aqueous solution of a water-miscible organic solvent, an aqueous solution of a water-soluble polymer, or mixtures thereof. Surrounding this central bore are two concentric annuli. From the inner annulus is extruded the dope solution. The dope composition emerges as a hollow tube which is prevented from collapsing over itself by the presence of the stream of intraannular fluid. As this process occurs, an extraannular fluid can be forced to flow over the outside surface of the fiber by utilizing the second, outer annulus which circumvents the first. This extraannular fluid is preferably a solvent system which is similar or the same as the intraannular solution used. Preferred nonlimiting examples of an extraannular fluid include water, alcoholic solvent, a water-miscible organic solvent, an aqueous solution of a water-miscible organic solvent an aqueous solution of a water-soluble polymer, or mixtures thereof. It is especially preferred that both fluids be maintained at a temperature above the LCST of the dope composition and are both able to serve as essentially the quenching media for the phase separated polymer system. In this manner, the inner and outer surfaces of the hollow fiber may be exposed to the same environment resulting in a more isotropic distribution of pore sizes than what would normally result in a process which does not enjoy the benefit of the outer curtain of extraannular fluid.

Using such a configuration in the process for manufacturing the hollow fiber membranes of the present invention, the variations in pore size brought about by the ambient air residing between the exit ports of the spinnerette and the normal stationary quenching/washing bath, which air is a different medium than the intraannular fluid and which is usually at a different temperature, is essentially eliminated. Thus the distance between the extrusion assembly and the stationary bath is no longer an important factor and a much greater flexibility to the placement of process equipment is subsequently achieved.

Perhaps more significantly, since the phase separation, extrusion, and quenching can be achieved in a very short span of time by employing the intra- and extraannular fluid configuration, the overall microscopic process for producing the hollow fibers more closely resembles the sequence of events which takes place during the simple flat sheet manufacturing process. Consequently, this invention is able to use essentially the same dope compositions, quenching media, and temperature settings used in preparing flat sheets, to produce hollow fibers with microstructures and characteristics similar to that of the flat sheets. Using the methods of this invention, a worker striving to develop better hollow fiber membranes may elect to experiment with and produce flat sheets because of their ease in manufacturing, while being confident that the results can be translated easily to hollow fiber structures. The benefits realized in terms of time, cost of materials, manpower, and capital costs can be significant.

Another advantage of the present invention is that expensive or relatively toxic extraannular fluids can be used to good effect employing only minimum amounts of liquid. Cost savings are again realized not only in purchasing materials but also in the subsequent disposal of waste.

Also, the use of the spinnerette assembly of the present invention offers a major improvement in manufacturing technique in that it enables one to obtain the desirable effect of high solvent content in the extraannular fluid, if desired, followed by rapid removal of the solvent on entering an aqueous quench bath. Thus, previously unobtainable membrane structures and control over structural features is now possible by the methods of the invention.

Accordingly, the role of the air gap in controlling the solvent evaporation time is largely eliminated. Thus, the distance between the spinnerette face and the quench bath becomes relatively unimportant. This distance becomes an important part of the process only if the kinetics of membrane formation is sufficiently slow or if the composition of the extraannular fluid compromises the structure of the membrane itself.

Furthermore, although the intra- and extraannular fluids may serve both to initiate the thermal phase separation and to quench the resulting microporous structure, the stationary washing/quenching bath still serves to partially quench and preserve the membrane structure. As mentioned above, the strong solvent is also washed away from the membrane in the wash process along with other contaminants. Preferably, the bath temperature should also be kept above the LCST of the dope composition.

Phase boundaries may naturally serve to define process temperatures. Typically, a temperature of about 10° C. above the LCST is employed in producing relatively isotropic microporous membranes with pores in the range of 1 μm in diameter. Dopes can be maintained in the single phase region of the phase diagram (e.g., at 60° C.) before reaching the spinnerette in the extrusion process, or equally useful, the dope may be caused to phase separate either in the dope lines or dope pot. The point up-stream of the spinnerette at which thermal phase inversion occurs does not seem to matter greatly, an observation which is contrary to the general teachings of the membrane art which teaches that dopes should be maintained in the single phase at all times until it emerges from the spinnerette. According to conventional wisdom, phase separation in any part of the spinning apparatus should be avoided because it normally results in irreproducible and inferior membrane properties (e.g., defects, closed cell matrix structure, and the like). It has been found, however, that the important consideration is that the dope attains a temperature equal to or greater than the LCST before or very soon after contacting quench media. Thus in the case of flat sheet casting, polymer dopes are preferably extruded in the single phase and quenched in about 80°–90° C. water. For hollow fibers, both the quench bath and spinnerette are preferably maintained at about 80°–90° C.

The hollow fibers which emerge from the quench bath are preferably further washed "on-line" in a series of Godet baths. A Godet bath consists of a pair of parallel drums partially submerged in a wash tank. The fibers are wrapped several times around these rotating drums, increasing the length of time that the fibers reside in the bath. Godet and wash bath temperatures are also important considerations with regard to membrane permeability and fine structure. For example, a commonly used washing temperature after the fiber has been taken off the spin line is about 60° C. (for approximately one day). However, if washing is done at room temperature instead such fibers may exhibit reduced hydraulic permeability compared with fibers washed at 60° C. These reduced Lp fibers, when subsequently washed at 60° C. or above show equivalent permeability to fibers which are washing at 60° C. immediately after being produced on the spin line.

In extruding preferred PES/PEO dope compositions a number of bore injection (intraannular) fluids can be employed to good effect. These include: water, water/solvent (e.g., NMP) mixtures, pure solvents (e.g., NMP), water soluble polymer solutions (e.g., PVA), gas (e.g., nitrogen), humidified gas, various non-solvents and liquids which are immiscible with components in the dope, according to one's ultimate goal. When making relatively isotropic microporous membranes with surface pores in the range of 1 μm, the preferred bore injection fluid is a water/NMP mixture.

Similarly, the extraannular fluid composition and flow rate can both be varied over a very wide range in order to manipulate the nature of the surface pores, or the degree of symmetry in the sub-structure. Again, for substantially isotropic structures, the intra- and extraannular fluids may be the same.

Skinned hollow fibers can be prepared by using appropriate quench solvents well known in the art (including water, water/solvent mixtures, alcoholic solvents, salt solutions, and the like). The skin may be prepared on the lumen surface or, alternatively, on the outer surface of the hollow fiber by employing a suitable intra- or extraannular fluid, however. Useful ultrafiltration (UF) membranes with unique pore size and distribution characteristics are thus produced. Other applications of these skinned fibers include auxiliary filtration, diagnostic uses, alcohol reduction, purification, and gas separation. It is important to remember that one skilled in the membrane art can take full advantage of the methods and apparatus described herein to make various adjustments and combinations in spinning conditions (e.g., nonsolvent as the intraannular fluid while using strong solvent as the extraannular fluid, operating at various temperatures, etc.) to produce a wide variety of hollow fibers with pore sizes ranging in the micron scale to tens of angstroms in size.

5.3.3 Charge-Modified PES Membrane Surfaces

Commercial 2.5 cm polysulfone membrane discs (Tuffryn membrane filter, HT-200, Gelman Sciences, Ann Arbor, Mich.) are washed with cold water three times to remove the water washables, and three times more with isopropanol to remove the isopropanol extractables. The membranes are then washed overnight to remove acetonitrile extractables. The membranes are then activated with 10% EGDGE in 0.6N NaOH for 4 hours to form pendant covalently bound epoxide groups. After washing the excess EGDGE with cold deionized water, some of the membranes are immersed in 2% HEC in 0.6N NaOH, others in 2% carboxymethyl cellulose (CMC) (Cellulose Gum-CMC, Type 7LF, Hercules Inc., Wilmington, Del.) in 0.6N NaOH, and still others in 2% poly(ethyleneimine) (PEI) (Molecular weight 70,000, Aldrich Chemicals, Milwaukee, Wis.). A control extracted Tuffryn membrane is also placed in deionized water. All the membranes are then placed in a water bath at 60° C. for 16 hours to commence covalent grafting. The membranes are then washed with hot deionized water at 60° C. in order to remove the unreacted water soluble polymers. The membranes are next tested for their ability to bind and elute human IgG using the standard protocol given in Example 6.4.2 of the copending and commonly assigned Application of Azad and Goffe entitled "Process For The Covalent Surface Modification Of Hydrophobic Polymers And Articles Made Therefrom" filed Oct. 17, 1988 and incorporated in its entirety by reference herein, except for the following differences. The human IgG is dissolved in the phosphate buffered saline with Tween 80 which has been diluted 1:10. The washings are also carried out using the same diluted buffer. The elution protocol is the same as given in said Example 6.4.2. The results of the elution are given in Table XIII.

TABLE XIII

Human IgG Eluted from HEC, CMC and PEI Treated Tuffryn Commercial Polysulfone Membrane, and Controls

| Sample | mg IgG eluted/mL* membrane volume |
|---|---|
| 1. HEC coated | 0.21 |
| 2. CMC coated | 0.86 |
| 3. PEI coated | 1.27 |
| 4. Control, uncoated | 0.24 |

*Results average of two sample.

The results suggest that charge-modified membranes (entries 2 and 3 in Table XIII) are better able to bind human IgG than a simple hydrophilic (HEC) surface.

5.3.4 Preparation of Modules Containing Modified Hollow Fiber Membranes

PES/PEO hollow fiber membranes (Batch No. 2300-6) are made as described in Example 6.8. Approximately 100, 18 inch fiber membranes are placed in a two liter beaker. The membranes are then washed in the normal manner with hot water at 95° C. for 16 hours, and then with 5N NaOH at 95° C. for 16 hours in order to maximize the surface functional end groups. Samples from the NaOH treated fiber are saved for analysis. The remaining fibers are then activated with EGDGE and grafted with HEC once (1X HEC) as described above. After washing with hot water, the fibers are divided into two groups. The first group is washed in cold water, while the second group is washed in acetonitrile. The second group of fibers is then transferred to cold water. Both groups of fibers are then given a second grafting of HEC, washed in hot water to remove unreacted HEC, and finally washed in cold water and acetonitrile as described above. This procedure is repeated once more, in order to produce a thrice HEC grafted (3X HEC) PES fiber. The samples are washed again in water and acetonitrile. Samples are saved at each stage of treatment for the determination of hydroxyl group concentration and non-specific binding, as well as permeability and Protein A coupling/human IgG binding and elution. The results of hydroxyl group and bovine serum albumin non-specific binding are given in Table XIV.

TABLE XIV

Total Hydroxyl Group Concentration (OH Conc.) and Non-Specific Binding (NSB) of PES/PEO Hollow Fibers (2300-6) after Various Surface Treatments

| Sample | —OH Conc. | NSB | —OH Conc. | NSB |
|---|---|---|---|---|
| I. After NaOH Treatment | 2.3 | 1650 | | |
| II. HEC Coated | Water-Washed Only | | Acetonitrile-Washed | |
| 1. Once coated | 17.3 | 67 | 21.2 | 62 |
| 2. Twice coated | 24.6 | low* | 22.2 | low* |
| 3. Thrice coated | 28.1 | low* | 29.3 | low* |
| III. Control Membrane Hydrophilic Durapore (0.22 micron) | 103.2 | low | | |

*The NSB was very low and was difficult to assign a quantitative value. The —OH concentrations are expressed as μmol —OH/mL membrane volume and the NSB values are in μg monomeric BSA/mL membrane volume.

The fibers (2300-6) have an initial permeability in the $900 \times 10^{-9}$ cm$^3$/dyne sec range before coating the HEC. After grafting three times with HEC, the permeabilities are still in the 290 to $300 \times 10^{-9}$ cm$^3$/dyne sec range. This result again shows the efficiency of the present invention in generally limiting the covalent grafting onto the surface layers, while not plugging the pores of the membrane.

The fibers which have been coated three times with HEC, with acetonitrile washings in between, are then FMP activated, in a beaker, and dried in air. A hollow polysulfone module is packed with 0.5 mL of the membranes. Recombinant Protein A is then coupled to the contents of the module. The module is then tested for the ability to take up human IgG from the phosphate buffer solution containing IgG. After loading of human IgG and washing off the unbound IgG, the module elutes 4.0 mg of IgG, giving a membrane capacity of 8.0 mg IgG/mL membrane volume.

5.3.4.1 Immunoaffinity Purification of Factor VIII (FVIII)

Two hundred and sixty, 22 inch PES/PEO hollow fiber membranes (Batch No. 2400-5) prepared according to the procedure described in Example 7.6 of copending application of Azad and Goffe entitled "Process For The Covalent Surface Modification Of Hydrophobic Polymers And Articles Made Therefrom" filed Oct. 17, 1988, and with a hydraulic permeability of $500 \times 10^{-9}$ cm$^3$/dyne sec, are soaked in two liters of hot 95° C. water for 16 hours. The fibers are then autoclaved with steam at 121° C. for 15 min. They are then soaked in acetonitrile at room temperature for 16 hours, washed with cold water and treated with 0.6N NaOH containing 10% EGDGE for 4 hours. After washing the excess EGDGE with cold deionized water, the fibers are soaked in 0.6N NaOH containing 2% HEC at 75° C. for 3 hours and then washed with hot deionized water at 55° C. (to remove the unreacted HEC and excess NaOH). The fibers are then treated with FMP and air dried. The hydraulic permeability of the FMP-activated fibers is $138 \times 10^{-9}$ cm$^3$/dyne sec with an average mean pore diameter of 0.30 μm as measured by a Coulter® Porometer. The fibers also have a hydroxyl concentration of 32.4 μmol/mL membrane. A hollow fiber module with an internal volume of 1.5 mL, is then made by packing several fibers treated as above into a polysulfone module. The final fiber membrane volume is 0.5 mL.

A NaHCO$_3$ buffer solution (pH 8.1, 15 mL) containing 0.3 mg of anti-FVIII antibody/mL is prepared by diluting anti-FVIII antibody (received as ascites fluid ESWF 7 from American Diagnostic, New York, N.Y., and purified using a Protein A column) with bicarbonate buffer, concentrating the resulting solution by ultrafiltration, and diluting the concentrated antibody to the appropriate concentration. The antibody solution is then recirculated at room temperature for 16 hours through the fiber module using a peristaltic pump. The loosely bound antibody is removed by washing the module with sodium bicarbonate buffer. Unreacted FMP groups are extinguished using the procedure described for Protein A in Example 6.4.1 of copending application of Azad and Goffe entitled "Process For The Covalent Surface Modification Of Hydrophobic Polymers And Articles Made Therefrom" filed Oct. 17, 1988, except for the use of the pump to recirculate solvents and reagents. The module containing covalently attached antibody is then tested for its ability to pick up FVIII as described below.

FVIII concentrate (1.3 U/mg protein, Hyland Laboratories, Inc., California) is diluted to 0.76 U/mL with 0.015$\underline{M}$ citrate buffer (pH 7.0) containing 0.15$\underline{M}$ NaCl. The diluted buffer solution is passed once through the fiber membrane module at a flow rate of 2 mL/min. A total of 22.9 mL (17.3 U) of buffer is passed through the module. The filtrate is saved for protein content analysis. The device is then washed with a buffer containing 0.015$\underline{M}$ sodium citrate and 0.15$\underline{M}$ NaCl (pH 7.0) until the absorbence at 280 nm of the washings is negligible indicating that no more loosely bound protein is coming off the module (ca. 30 mL). The bound FVIII is then eluted with a buffered solution containing 1$\underline{M}$ KI, 1$\underline{M}$ lysine, 20 m$\underline{M}$ imidazole, and 5 m$\underline{M}$ CaCl$_2$ (pH 6.5). The filtrate and eluate are then assayed separately for FVIII:C activity using Stratchrom® FVIII:C Antihemophilic Factor Chromogenic Assay (Diagnostica Stago, 6 ter, rue Denis Papin, 92600 Asnieres, France). The filtrate is found to contain 3.3 U, indicating that the 81% of the applied FVIII is retained by the module. The eluate fraction (3.8 mL) contained a total of 8.0 U of FVIII:C activity corresponding to an overall recovery of 46% FVIII:C activity. The balance of the FVIII initially applied is assumed to be in the buffer washings. Specific FVIII:C activities of starting material (1.3 U/mg protein) and eluted FVIII (150 U/mg protein) are determined based on FVIII activity and protein concentration as measured by the Lowry protein assay, and yielded a purification factor of 115. The above procedure is not optimized and could, doubtless, be improved by lowering the flow rate, recirculating the buffered protein solution, or changing the buffer constituents, for example.

It is understood that the invention described and claimed herein is not limited to the immunoaffinity purification of FVIII as the ligate. The isolation and purification of other ligates, especially those of biological significance, by methods similar to those described above are within the scope of this invention. Examples of ligates that may be purified by immunoaffinity and biospecific recognition include, but are not limited to, tissue plasminogen activator, human coagulation factor IX, hormones, interleukins, other human and mammalian proteins, and others described previously in Section 5.

5.3.5 Modification of Commercial Flat Sheet and Hollow Fiber Membranes

Commercial polysulfone flat sheet and hollow fiber membranes are modified as follows to demonstrate the general applicability of this invention.

The 0.2 micron polysulfone hollow fiber membrane (Model CFP-2-E-4, AG Technology Corp., Needham, Mass.) is removed from the microfiltration module, and washed for two weeks with isopropanol in order to remove isopropanol extractables. The commercial 0.45 micron flat sheet polysulfone membrane (HT-450 Tuffryn, 25 mm diameter, Product No. 66221, Gelman Sciences, Ann Arbor, Mich.) is first washed with water to remove water extractibles, and overnight with isopropanol to remove isopropanol extractables. A part of the membranes are also washed overnight for 16 hours to remove acetonitrile extractables.

Part of the membranes from each treatment is then grafted with HEC as described earlier after first treating with 10% EGDGE in 0.6N NaOH for 16 hours. The samples are then washed with hot water and saved for hydroxyl group determination and BSA-NSB. Table XV of copending application of Azad and Goffe entitled "Process For The Covalent Surface Modification Of Hydrophobic Polymers And Articles Made Therefrom" filed October 17, 1988, gives the results of the —OH group concentration and BSA-NSB of these membranes at various stages of the surface treatment. All the measurements are carried out in one experimental matrix with the commercial control membrane.

5.4 Membrane Process and Apparatus Specification

Figure 2:
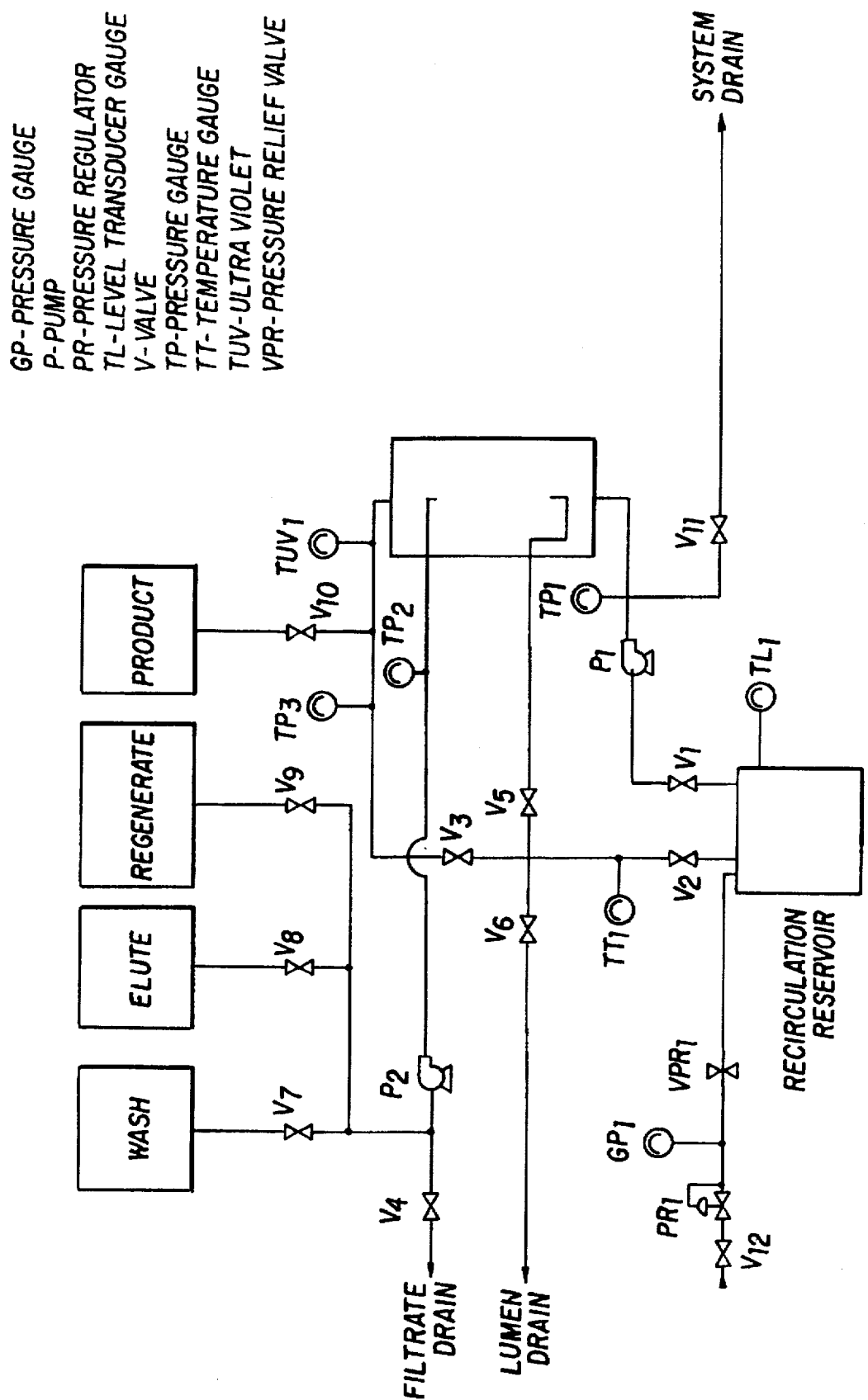
FIG. 2 illustrates the preferred large-scale membrane affinity apparatus including pump means, valve means, piping means and solutions along with indications of material flow directions through the apparatus.

The apparatus can be configured at an scale required to achieve the operation steps. Four operation steps are preferred: (1) LOAD; (2) WASH; (3) ELUTE and (4) REGENERATE. The principles of scale-up will be described below. This will be followed by a detail description of the operating steps in conjunction with the schematic diagrams presented in FIGS. 1 and 2.

Scale-up of the membrane process is based on the constraints of mass transfer and pressure drop. The relationship of variables used for constraints on mass transfer is defined by equation 1. This expression is used to define the system scale or module size based on: 1) the knowledge of the volume of fluid to be processed per day, Q: 2) morphology of the porous membrane structure; 3) diffusivity of the target molecule; and 4) value of the Peclet number for favorable capture. Equation 1 becomes $$V_0 = \frac{Q_L * t_D}{Pe} \quad \text{Equation 2}$$

In this design equation Pe can be specified as 0.01, $t_D^2/D$, and $Q_L$ is the LOAD step flow rate based on Q. The result of this calculation is a value for the membrane void volume, $V_0$, where:

$$V_m = V_o / \text{Porosity fraction} \quad \text{Equation 3}$$

$V_m$ is the volume occupied by the membrane. Given a membrane with defined wall thickness, internal diameter (or width) and length, the frontal surface area of the membrane required is defined.

Pressure drop constraints on the design scale-up result from the need to provide uniform perfusion of the membrane down the length of the channel. To achieve this it is preferred to constrain the ratio of transmembrane to translumen pressure drop to less than 0.10. This constraint can further change dimension of the flow channel and/or membrane surface area.

Three scales of module apparatus can be defined with the design process outlined above. This does not preclude other process scales that can range over any volume that is to be processed in a required period of time.

Membrane module size can be defined as 1.5 mL, 30 mL or 150 mL, referring to the approximate interior volume in the module itself. Hollow fiber membrane typically occupies ⅓ of the total module volume. A 1.5 mL laboratory scale module apparatus according to this invention can process 5 Liters of feedstream per day, corresponding to a monoclonal antibody product yield in the 200 mG range. A 30 mL pilot scale membrane module apparatus according to this invention can process 100 liters of feedstream daily. The 150 mL process scale membrane apparatus according to this invention will process 500 liters daily. Similar membrane process apparatus can be designed to process 2,000 to 10,000 liters per day. It is within the scope of this invention that the interior volume of the module can range from 1 mL or lower to 10 liters or higher, preferably 1.5 mL to about 1000 mL.

The membrane process apparatus at any scale is designed to occupy a space smaller than required for column technology that would process equivalent volumes of feedstream. Control and data aquisition are preferably automated. The operator interface is a power-on switch, start/ stop buttons and computer interface that provides access to system control for changing operating conditions. The computer and/or micro processor based controller actuates solenoid valves and ramp pumps up to desired flow rates.

Events are timed open loop intervals or decisions based on any combination of absorbence UV value(s), pressure(s), conductivity, reservoir level(s) or temperature. The decision can be based on either magnitude or time based derivative and can be used to start and stop steps or switch valves.

Filtrate and recirculation flow rates are preferably controlled by peristaltic pumps. The pump speeds are preferably set on an operator inter face but can be based on pressure feed back control.

The systems can be operated under sterile conditions using disposable tubing and pinch valves in the case of the smaller scale membrane process apparatus and Steam-In-Place technology in the case of the process scale membrane process system apparatus. The larger scale process system is pressurized during all phases of the operation. This is achieved by adjusting pressure in the head space of the reservoirs. The system is operated under positive pressure to insure a net positive suction head for the filtrate pump.

Tanks with cooling jackets and recirculation loop preferably have temperature probes.

Tank levels are preferably monitored with capacitance probes.

Materials in contact with the fluid streams are preferably non-reactive corrosion resistant and biocompatible, such as polypropylene, silicone, polysulfone, polycarbonate, teflon, norprene, C-Flex (thermoplastic elastomer), and electropolished 316L stainless steel. Flexible tubing is connected by barbs to luers and fittings and used in the smaller scale system. The peristaltic pumps in both lab and large scale systems use flexible tubing. Tubing in the large scale system is preferably stainless steel.

In the 1.5 and 30 ml scale membrane affinity absorption systems (FIG. 1) the apparatus is preferably operated in the sequence which follows (wherein "V" is a valve means and "P" is a pump means):

Step 1. LOAD

Purpose of this step is to load the membrane structure with the target protein. Cross Flow Filtration is used in this step. The filtrate pump regulates flow rate and volumetric throughput.

A. Recirculation Flow—50 to 100 ml/min. For the 1.5 ml module is preferred.
      250 to 2000 ml/mn for the 30 ml module.
      P1 supples flow to Affinity Modules
      V4 is open
      V8 directs flow to V9
      V9 directs flow to Recirculation reservoir
   B. Filtrate Flow—2 to 20 ml/min. for the 1.5 ml module preferred.
      40–400 m/min for the 30 ml module
      P2 regulates flow through the membrane in the Affinity Module
      V5 directs flow to V6
      V6 directs flow to P2
      V7 directs flow to Filtrate Drain Step 2. WASH Purpose of this step is to remove unwanted and unbound proteins from the Affinity Module and membrane.

P1 stops and V4 closes

A. Shell Flush
      P2 pumps buffer to Shell side of module
      V1 directs flow to V6
      V6 directs flow to P2
      V7 directs flow to Affinity modules
      V5 directs flow to Shell Drain
   B. Lumen Wash
      V4 is open, V5 stops flow to drain
      P2 pumps buffer to Shell side of module
      V1 directs flow to V6
      V6 directs flow to P2
      V7 directs flow to Affinity modules
      V4 directs flow to V8
      V8 directs flow to Lumen Drain Step 3. ELUTE The purpose of this step is to provide for uniform elution of the target molecule from the membrane structure. In the Product Elution part of this step it is preferred to use Back Flushing.

A. Shell Flush—Same as above (in IIA), V2 provides buffer.
   B. Product Elution—Same as Lumen Flush (in IIB) except:
      V8 directs flow to V9
      V9 directs flow to Product Reservoir

STEP 4. REGENERATE

The purpose of this step is to re-equilibrate the membrane to conditions suitable for loading.

A. Shell flush—same as wash, V3 provides buffer
   B. Lumen wash—same as wash, V3 provides buffer In a Large Scale System (FIG. 2) the apparatus is preferably operated in the sequence which follows (similarly "V" is a valve means and "P" is a pump means):

STEP 1. LOAD

Purpose of this step is to load the membrane structure with the target protein. Cross Flow Filtration is used in this step. The filtrate pump is reversable and regulates flow and volumetric throughout V1, V2, V3 and V4 are open. All other valves are closed.

A. Recirculation Flow—5 to 10 l/min., preferred for one 150 ml membrane module
      P1 supplies flow to Affinity Modules
   B. Filtrate Flow—0.2 to 2 l/min., typical.
      P2 Regulates flow through the membrane in the Affinity Module
      V4 directs flow to Filtrate Drain
      PR1 Supplies positive bias pressure to the system and assures net positive suction head to P2.

STEP 2. WASH

Purpose of this step is to remove unwanted and unbound proteins from the Affinity Module and membrane.

P1 stops and V1, V2, V3 and V4 closes

A. Shell Flush
      P2 pumps buffer to Shell side of module
      V5, V6 and V7 are opened
      V5 directs flow to V6
      V7 directs flow to P2
      V6 directs flow to Drain
   B. Lumen Wash
      V5 is closed, V3 is opened
      P2 pumps buffer to Shell side of module
      V3 directs flow to V6
      V6 directs flow to Drain

STEP 3. ELUTE

The purpose of this step is to provide for uniform elution of the target molecule from the membrane structure. In the product elution part of this step it is preferred to us Back Flushing is used.

A. Shell Flush—Same as above (in IIA), V8 provides buffer
   B. Product Elution—Same as Lumen Flush (in IIB) except:
      V3 is closed, V10 is open
      V10 directs flow to Product Reservoir

STEP 4. REGENERATE

The purpose of this step is to provide for uniform regeneration of the membrane hollow fibers. After regeneration of the membrane hollow fibers, the cycle can be repeated.

A. Shell Flush—same as above (in 2A), V9 supplies buffer
   B. Lumen Flush—same as above (2B) wash but again, V9 supplies the buffer The examples above detail the preferred embodiment of the membrane probes apparatus. This apparatus utilizes crossflow filtration in the load step and membrane backflush in the wash, elute and regeneration steps. It is also within the scope of the invention that crossflow filtration can be eliminated, thereby creating dead end filtration where the entire volume of the feedstream passes through the membrane. It is also within the scope of this invention to eliminate backflushing by flowing solutions in the wash, elute and regeneration steps entirely in the direction of the load step operation.

Additional preferred operational specifications specific to the large or process scale apparatus are described below. The process scale affinity apparatus should be self-draining and free of cracks or crevices. These specification are scalable to the 1.5 and 30 ml membranes process apparatus.

The preferred performance specifications for the large scale apparatus are set forth in Table 1.

TABLE I

| | |
|---|---|
| IgG Inlet Concentration | 0.05 ± 0.02 mg/ml |
| IgG Outlet Concentration | 0.75 ± 0.25 mg/ml |
| IgG Binding Capacity | 10 ± 4 mg/ml MV |
| Total IgG Binding Capacity | 450 ± 240 mg |
| IgG Purity | >80% |
| IgG Specificity | <1 mg serum protein/ml MV |
| Protein A Binding Capacity | 10 ± mg/ml Mv |
| Total Protein A Binding Capacity | 450 mg± |
| Cycles/Module | 75 |

The preferred operating flow rates, pressures and temperatures are specified in Table II.

TABLE II

| Pressures | Min. | Max. | Base Case |
|---|---|---|---|
| Static Operating | 1 | 10 | 5 psig |
| Transmembrane | 1 | 3 | 2 psig |
| Temperatures | | | |
| Product & Recycle Tanks | | | 4° ± 2° C. |
| Inlet Buffers | | | 4° ± 2° C. |
| Loop Gradient | | | 2° C. max |
| Flow Rates | Min. | Max. | Base Case |
| Filtrate | 1 | 6 | 3.5 L/min |
| Recycle | 10 | 20 | 15 L/min |
| Conversion | 10% | 30% | 25% |
| Buffers | 1 | 5 | 3 L/min |

The volumes preferably utilized in the large scale apparatus are set forth below in Table 3.

TABLE III

| | Min. | Max. | Base Case |
|---|---|---|---|
| Adsorption | 4 | 14 | 9 L |
| Wash | 1 | 5 | 3 L |
| Elution | 1 | 5 | 3 L |
| Regeneration | 1 | 5 | 3 L |
| Adsorption/8 hour shift | 80 | 560 | 360 L |
| Buffer/8 hour shift | 80 | 480 | 280 L |
| Adsorption/Batch | 300 | 1050 | 675 L |
| Adsorption/Week | 1500 | 9450 | 4725 L |

The large scale affinity apparatus module specifications are preferably as follows:

| | |
|---|---|
| Volume | 150 mL |
| Number per system | 4 |
| Material of Construction | Polysulfone |
| Pressure | 30 psig |
| Temperature Limit | 126° C. |
| Connections | 1½ Triclamp |

The preferred fiber specifications for use in the affinity apparatus are as follows:

| | |
|---|---|
| Effective Length | 13 ± 0.5 cm |
| Total Length | 15 ± 0.5 cm |
| ID | 1000 ± 5.0 μm |
| OD | 1600 ± 5 μm |
| Porosity | 0.8 + .05 / −.35 |
| Pore Size | 0.6 μm + 1.0 / −0.3 |
| Membrane Volume/Fiber | 0.159 ± 0.012 mL± |

-continued

| | |
|---|---|
| Fibers/Module | 285 ± 15 |
| Total Membrane Volume/Module | 45 ± 5 ml |
| Surface Area/module | 1163 ± 155 cm$^2$ |
| Dynamic Pressure Drop | 2–7 psig |

The use of the affinity apparatus in carrying out an affinity purification procedure is illustrated by the following example:

6.0 EXAMPLES

6.1 Membrane Affinity Purification of Fibronectin From Blood Plasma

Purification of fibronectin (FN) from blood plasma was carried out in accordance with the general method described by Miekka, et al. (Thromb. Res. 27, 1–14, 1982) using flat sheet HPC-coated PES/PEO membranes containing immobilized porcine skin gelatin (Sigma Type I). Membrane disks were inserted in a plastic filter holder (2.5 cm diameter), which was placed in the experimental apparatus illustrated in FIG. 6. Convection of plasma and buffer solutions through the membrane device was controlled by a peristaltic pump. Absorbence of effluents at 280 nm was monitored using a UV detector installed upstream of a fraction collector. Transmembrane pressure was measured using an on line pressure transducer.

In a typical affinity membrane-based FN purification run (FIG. 7), 4.6 mL of blood plasma was loaded onto a 0.34 mL membrane device. After washing the membrane with equilibration buffer and 1M NaCl, FN was eluted by lowering the pH to 5.5. All steps were performed at a flow rate of 1.0 mL/min., corresponding to a membrane residence time of approximately 15 seconds. Analysis of filtrate fractions for FN using a commercial immunoturbidimetric assay (Boehringer Mannheim) indicated that essentially all of the FN was removed from the feed plasma. The amount of purified FN isolated was 0.34 mg, or 26% of the starting FN.

Samples of purified FN and FN-depleted plasma were analyzed by SDS-PAGE on 8–25% gradient gels (Pharmacia) visualized by silver staining (FIG. 8). The FN band near 230,000 daltons evident in the starting plasma (b) and the FN standard (E) is nearly absent in the FN-depleted plasma (C). The low pH eluate (D) is nearly pure FN, containing trace amounts of serum albumin. The percent purity of the eluted product was determined by comparing the concentration of FN determined by immunoturbidimetry with the protein concentration determined by A280 (based on a value of 12.8 for the absorbence of a 1% FN solution). The value obtained for affinity membrane purified FN is 93%.

The effect of plasma loading rate on efficiency of FN uptake was examined using the experimental setup described above. Plasma (8.8 mL; 25.9 membrane volumes) was passed through the membrane device at flow rates of 0.3, 1.0, 3.0 and 6.0 mL/min. (corresponding to residence times of 51, 15, 5.1 and 2.6 seconds, respectively). At all of the flow rates tested, it was found that at least 6.0 mL (18 membrane volumes) of FN-depleted plasma could be collected prior to emergence of appreciable quantities of unbound FN.

6.2 Immunoaffinity Purification of Factor VIII (F.VIII)

A 1.5 mL hollow fiber affinity module containing covalently attached monoclonal antibody against F.VIII was loaded with F. VIII concentrate diluted to 0.76 U/mL in 0.015M citrate, 0.15M citrate, 0.15M NaCl pH 7.0 at a flow rate of 2 mL/min. After loading of 22.9 mL (17.3 U), the device was washed with 0.015M citrate, 0.15M NaCl pH 7.0 until the absorbence at 280 nm of the washings was negligible (30 mL). The bound F.VIII was then eluted with a buffered solution containing 1M KI, 1M lysine, 20 mM imidazole, 5 mM CaCl$_2$ pH 6.5. Pooled filtrates and eluates were assayed for F.VIII:C activity. The filtrates were found to contain 3.3 U, indicating that the device had captured 80% of the applied F.VIII. The eluate fraction contained 8.0 U.F. VIII: c activity for an overall recovery of F.VIII activity of 46%. Specific F.VIII:C activities of starting material and eluted F.VIII were determined based on F.VIII activity and protein concentration as measured by the Lowry assay. Comparison of these values yielded a purification factor of 115. These data are summarized below:

TABLE I

| Fraction | F.VIII Activity U/mL | Protein mg/mL | Spec Act mg/mL | Purif. factor |
|---|---|---|---|---|
| Starting material | 0.76 | 0.60 | 1.3 | — |
| Eluate | 2.1 | 0.014 | 150 | 115 |

Commercial F.VIII concentrate was obtained from Hyland Laboratories, Inc. MAB against F.VIII complex was obtained from American Diagnostica. This monoclonal antibody was produced in ascited fluid and purified on Protein-A Speharose gel; its designation is American Diagnostica ESVWF1, indicating that the monoclonal antibody recognizes the von Wildebrant's portion of the Factor VIII complex.

6.3. Immunoaffinity Purification of F. VIII from Blood Plasma

A. 1.5 mL affinity module containing monoclonal antibody against F. VIII similar to the device described in the above example was loaded with untreated blood plasma at a flow rate of 2 mL/min. After loading 50.6 mL plasma (50.6 Units F. VIII:C activity), the device was washed and eluted as described above. Pooled filtrates and eluates were assayed for F. VIII:C activity as described above. The filtrates were found to contain 8.1 Units (16% of activity loaded), indicating that 84% of the applied F. VIII had been captured. The eluate fraction contained 16.9 Units (33% of activity loaded). Overall recovery of F, VIII:C activity was 49% Specific F, VIII:C activities of the eluate fraction and the starting plasma were determined based on the F, VIII:C assay results and protein concentrations are measured by the Lowry assay. Comparison of initial and final specific activity values yields a purification factor of 56. These results are summarized below:

| Fraction | F.VIII:C Activity (U/ml) | Protein (mg/mL) | Specific activity (U/mg) | Purification factor |
|---|---|---|---|---|
| Starting plasma | 1.0 | 72 | 0.014 | — |
| Eluate | 3.2 | 4.1 | 0.78 | 56 |

6.4 Protein A Membrane-Mediated Capture of Human IgG

The ability of affinity membranes to efficiently capture target proteins at loading rates corresponding to residence times of a few seconds was assessed using Protein A as the affinity ligand and human IgG as the target protein, Flat sheet affinity membranes containing immobilized Protein A were inserted in a plastic filter holder (2.5 cm diameter) and placed in the experimental setup shown in FIG. 6. The total membrane matrix volume contained in the device was 0.2 mL; the total static IgG capacity of the device was 0.76 mg (3.8 mg/mL membrane matrix volume), The bind/elution cycle was composed of (i) passage of 11.6 mL of a solution of 0.05 mg/mL human IgG (Sigma) in phosphate buffered saline pH 8.0 (PBS) through the device at a preselected flow rate (corresponding to an IgG loading of 2.9 mg/mL membrane matrix volume—76% of the static capacity), (ii) washing of the device with PBS until the absorbence of the washings at 280 nm was negligible and (iii) elution of the captured IgG with 0.1M citrate buffer pH 3.0. The efficiency of capture during the IgG loading step was assessed in the flow rate range from 0.25 to 5.0 mL/min. All other steps were performed at 0.5 mL/min. The IgG capture efficiency at each loading rate was assessed by determining the amount of IgG in the citrate eluate fractions using the Lowry protein assay. The Table below indicates that at an IgG loading of 76% of the device static capacity and at flow rates as high as 5.0 mL/min (corresponding to a fluid residence time of 1.8 sec), at least 75% of the applied IgG was captured.

Protein A Membrane-Mediate
IgG Binding and Elution
Effect of IgG Loading Rate

| | Loading Rate | | Fluid Res. | IgG Eluted | |
|---|---|---|---|---|---|
| Run# | (mL/min) | (matrix vol/min) | Time (sec.) | (mg/mL matrix) | % of applied |
| 1 | 0.25 | 1.3 | 36 | 2.6 | 90 |
| 2 | 0.50 | 2.5 | 18 | 2.6 | 90 |
| 3 | 2.5 | 12.5 | 3.6 | 2.4 | 80 |
| 4 | 5.0 | 25.0 | 1.8 | 2.1 | 75 |

Matrix volume: 0.2 mL
IgG applied per cycle 2.9 mg/mL matrix
Feed IgG conc.: 0.05 mg/mL
Total IgG cap. (static): 3.8 mg/mL matrix

6.5 Protein A Mediated Capture of a Monoclonal Antibody From Cell Culture Supernatant The ability of affinity membranes to efficiently capture target proteins from complex mixtures at high loading rates was assessed using Protein A as the affinity ligand and a monoclonal antibody as the target protein. In this case, the Protein A was immobilized in 1.5 mL hollow fiber module, which was then attached to the automated lab-scale affinity system described in Section 5. The feed solution was a serum-free cell culture supernatant containing 0.055 mg/mL of the desired monoclonal antibody along with contaminating proteins that were either produced by the cells or initially present in the media. Loading was performed in the cross-flow mode with a feed flow rate of 50 mL/min and filtrate flow rates ranging from 2.6 to 16 mL/min 9.2 to 1.5 seconds). The amount of cell culture supernatant loaded per cycle corresponded to either 2.9±0.1 mg monoclonal antibody per mL matrix volume (about 30% of the static capacity of the device for the target monoclonal antibody) or 9.0±0.4 mg/mL matrix volume (about 30% of the static capacity). The effect of filtration rate and monoclonal antibody loading on capture efficiency was determined by collecting the filtrates generated during each cycle and assaying for the presence of the monoclonal antibody using the HPLC method outlined by Hammen et al. (BioChromatography 3, 54–59, 1988). Comparison of the filtrate monoclonal antibody concentration with that of the feed solution yielded the percent capture efficiency. The results obtained in the following Table) indicate that at device loadings as high as 100% of the device static capacity and at fluid residence as low as 1.5 sec, over 80% of the applied target protein was captured.

Protein A Membrane-Mediated
Capture of MAb from Cell Culture Supernatant

| Amount loaded (mg/mL matrix) | Flow rate (mL/min) | $t_r$ (sec) | Capture efficiency (%) |
|---|---|---|---|
| 2.9 ± 0.1 | 2.6 | 9.2 | 92.2 |
| | 5.3 | 4.5 | 91.9 |
| | 10.7 | 2.2 | 90.8 |
| | 16.0 | 1.5 | 89.6 |
| 9.0 ± 0.4 | 2.6 | 9.2 | 85.9 |
| | 5.3 | 4.5 | 86.1 |
| | 10.7 | 2.2 | 84.0 |
| | 16.0 | 1.5 | 83.3 |

6.6 Protein A Membrane Mediated Purification of Monoclonal Antibody From Cell Culture Supernatant Purification of a target protein from a complex mixture in a rapid, multicyclical fashion was demonstrated using a 1.5 mL hollow fiber module containing immobilized Protein A attached to the automated lab-scale affinity system described in Section 5.1. The target protein was murine monoclonal antibody which was present in cell culture supernatant at a concentration of 0.039 mg/mL. Each bind/elution cycle comprised the following:

| LOAD: | Recirculation Flow-50 mL/min<br>Filtrate Flow-12 ml/min<br>Amount loaded per cycle-100 mL; 7.8 mg MAb/mL matrix |
|---|---|
| LUMEN WASH: | Buffer-PBS pH 8.0<br>Flow rate-20 mL/min<br>Volume-40 mL |
| SHELL ELUTE: | Buffer-0.1 n citrate pH 3.0<br>Flow rate-10 mL/min<br>Volume-10 mL |
| LUMEN ELUTE: | Buffer-0.1 n citrate pH 3.0<br>Flow rate-4.0 mL/min<br>Volume-24 mL |
| SHELL REGEN: | Buffer-PBS pH 8.0 + 0.1% Tween 80<br>Flow rate-10 mL/min<br>Volume-10 mL |
| LUMEN REGEN: | Buffer-PBS pH 8.0 + 0.1% tween 80<br>Flow rate-10 mL/min<br>Volume-20 mL |

The time for each individual cycle was 27 minutes. A total of 20 cycles were performed in which 2000 mL of cell culture supernatant was processed (FIG. 9). The amount of monoclonal antibody recovered was estimated by measuring the absorbence of the eluates at 280 nM and calculating the product concentration using $\epsilon 280=1.1$. Of the 78 mg monoclonal antibody initially present in the cell culture supernatant, 64 mg was recovered in a volume of 300 mL—indicating a product recovery of 82% and a concentration factor of 5.4. SDS-PAGE analysis of samples generated in this manner indicated that all contaminating proteins were removed from the purified product and that filtrates were essentially depleted of target monoclonal antibody.

6.7 Dope Preparation and Polymer Drying Procedure

The dope preparation procedure involves weighing and pretreating the two polymers employed in the blend. PES, which is also known as Victrex (by ICI America, grade 5200P, obtained in 15 kg bags), is dried in an oven at 150° C. for 3 h then allowed to cool to 60° C. for several hours more. The total time of heating in the oven is not less than about 24 h. PEO (Polyox 301, MW 4000 kD, by Union Carbide Corp., obtained in 140 lb drums) is pretreated in a vacuum oven at room temperature for about 24 h. Care is taken not to leave the pretreated polymers in the open air for extended periods before adding them to the mixer.

Both NMP (i.e., N-Pyrol, Cat. No. 1-3-72755/000 & 5-72, by GAF Chemicals Corp., obtained in 55 gal drums) and glycerin (by Baxter Scientific Product Group, Mallincrodt, catalog # 5092-4, Analytical Reagent) are used as received, but precautions are taken to minimize the uptake of atmospheric moisture by adding them to the mixer immediately after removal from the respective containers. Their containers should be closed tightly when they are not in use.

Mixing Procedure

NMP (2812 g) and glycerin (1128 g) are pre-mixed in a 1 gal container before adding them to a Ross (model PVM2) mixer at room temperature. The Ross mixer is fitted with a source for purging with nitrogen. The inert atmosphere is maintained over all liquids until the PEO has been added. On applying pre-mixed NMP/glycerin to the Ross mixer two of the mixing blades are started: the anchor blade at 135 rpm, and the disperser blade at 3,500 rpm. PEO (360 g) is added while mixing at room temperature over the period of about one minute. A 500 gram portion of NMP is then added to make a total of 3312 gram NMP in the dope. At this point the disperser blade is switched off and Mokon heat exchange unit is set at 120° C. After 3 h of mixing, the PES (1200 g) is added over the space of 2–3 minutes, and the temperature is noted with the anchor blade maintained at 135 rpm. After an additional 18 h, a steady decrease in temperature is initiated by setting the Mokon at 60° C. Within about 1.5 h of making this temperature change, the dope usually attains a temperature of about 75±5° C., at which time a vacuum is gradually applied to de-gas the mixture. Full vacuum is usually achieved within 15 min and is maintained for a further 5 min. The mixer is then switched off while continuing to de-gas A vacuum is maintained for 1–2 min longer before introducing nitrogen to re-establish atmospheric pressure in the mixing vessel at 60° C.

This preparative procedure typically results in a dope viscosity of about 100,000 (±20,000) cps at 60° C. However, occasional deviations from the norm occur which do not appear to result in any ill effects in membrane properties. Such a dope has phase boundaries at about 78° C. (LCST) and about 57° C. (UCST), as shown in FIG. 10.

6.8 Hollow Fiber Spinning of Relatively Isotropic Microporous Membranes Primarily For Affinity Applications A dope is prepared as outlined above and is found to have a viscosity at 60° C. of 123,000 cps. This dope is extruded through the co-extrusion spinnerette schematically represented in FIG. 11. Spinnerette temperature is maintained at 80° C. throughout the duration of the experiment. Other fixed parameters preferably include:

dope pump speed - - - about 70 rpm
quench bath temperature - - - about 90° C.
quench bath composition - - - Deionized (DI) water intraannular fluid composition - - - about 70% NMP:30% DI water (v/v)

extraannular fluid composition - - - about 70% NMP:30% DI water (v/v)

intraannular fluid flow rate - - - about 30.2 (±1.2) mL/min.

first and second godet bath temperatures - - - about 42.5 (±2.5) °C.

Other parameters which may also be varied in this experiment are: air gap or spinnerette height above the quench bath (which results in a change in fiber take-up rate or the rate of fiber production in linear feet per minute) and extraannular fluid flow rate. The latter is varied from zero to 66 mL/min with spinnerette heights ranging from 3-7 inches. Note that the spin line contains only two godet baths. Results from this experiment are shown in FIG. 13 and in the table of data inserted as part of the figure for fibers designated 2500-1 through 11. A very pronounced dependence of membrane hydraulic permeability (Lp) for DI water on extraannular fluid flow rate is evident. Fiber 2500-1, with zero outer annular fluid flow is equivalent to a fiber produced with a conventional tube-in-orifice spinnerette.

This dependence of the Lp on the extraannular fluid flow rate is reproducible using a portion of the same dope as that used in FIG. 13 (See Table XVI for fibers designated 2600-1 through 9).

TABLE XVI

Hydraulic Permeabilities of Hollow Fibers as a Function of Extraannular Flow

| Fiber Sample | LP (× $10^{-9}$ cm$^3$/ dyne sec) | Extraannular Flow (mL/min) | Air Gap (inches) | ID (μm) | OD (μm) |
|---|---|---|---|---|---|
| 2600-1 | 13 | 0 | 2.5 | 1000 | 1600 |
| 2600-2 | 210 | 10 | 2.5 | 930 | 1520 |
| 2600-3 | 13 | 0 | 2.5 | 1040 | 1500 |
| 2600-4 | 296 | 10 | 2.5 | 1020 | 1610 |
| 2600-5 | 33 | 0 | 2.5 | 1040 | 1620 |
| 2600-6 | 337 | 10 | 2.5 | 950 | 1500 |
| 2600-7 | 23 | 0 | 2.5 | 1000 | 1580 |
| 2600-8 | 309 | 37 | 2.5 | 1000 | 1560 |
| 2600-9 | 9 | 0 | 3.5 | 1000 | 1600 |

Fiber sample 2600-6 is examined by electron microscopy and pores in the 1-3 μm range are observed on the two surfaces. Overall pore size distribution in the matrix of the approximately 300 μm fiber wall varies within the range of about 1-2 orders of magnitude, but the great majority of the pores are within 1 order of magnitude of each other in size. The results indicate that this membrane is an example of a substantially skinless relatively isotropic microporous membrane. By contrast, fiber 2600-5 (which is made minus the extraannular fluid) is a far more anisotropic microporous membrane structure.

Fiber 2600-6 and others from this batch are then autoclaved, hydrophilized by grafting a composite coating onto its entire internal and external surfaces, and successfully employed in affinity and bioseparation experiments. The 1.5 mL hollow fiber modules containing 0.5 mL membrane volume are covalently functionalized to attach Protein A ligand. The IgG capacity for such modules is determined to be 7 and 8 mg/mL (for modules #13 and #14 respectively), while non-specific binding of fetal calf serum proteins have a capacity of about 1 mg/mL. The non-specifically bound proteins are easily washed off the membrane surfaces due to the hydrophilicity. High loading capacities are achievable with this fiber because of the 300 micron wall thickness, while the high hydraulic permeability for DI water is retained both after hydrophilization and chemical activation. For example, modules #13 and 14 have Lp values of 314×10$^{-9}$ and 191×10$^{-9}$ cm$^3$/dyne sec, respectively. After Protein A ligand is applied the Lp value is 149×10$^{-9}$ cm$^3$/dyne sec for module #14.

A wide range of microfiltration and ultrafiltration applications can be addressed by these membranes (with or without further surface modification or hydrophilization), where the relatively low protein binding surfaces minimize fouling and plugging of the matrix. Of particular interest is the use of the relatively isotropic microporous fibers (e.g., fiber 2600-6) for cell separation. This separation of cells from accompanying liquid can be achieved at very high fluxes without catastrophic decay in hydraulic permeability, which is typically observed for commercially available hollow fibers. Some examples of such cell separation applications include: clarification of cell broth and conditioned media (where affinity binding and clarification may be combined to reduce the number of unit operations in protein purification), and separation of blood cells for medical applications.

The range of extraannular flow rate demonstrated in this example (i.e., FIG. 13), with the dope and extraannular fluid combinations spanning over five orders of magnitude difference in viscosity, is not possible with the modular spinnerette disclosed in U.S. Pat. No. 4,493,629.

6.9 Effect of Wash Time and Temperature

Hollow fibers are produced with an extraannular fluid from a dope having a viscosity of 108,000 cps at 60° C. Spin parameters employed in the experiment are detailed in Table XXII. After washing in water at about 60° C. overnight the average hydraulic permeability for DI water (based on three test modules) was determined to be 348×10$^{-9}$ cc/dyne sec for fiber sample 3000-1.

Similarly, another dope is prepared with a viscosity of 118,000 cps at 60° C. and hollow fibers 3100-1 through -5 are produced under substantially the same conditions as fiber 3000-1 above. All these fiber samples are produced under identical spinning conditions to provide large quantities of fibers with the same Lps. Some of these membranes (collection batch 3100-2 to -5) are employed in a series of washing experiments in which both washing time and temperature are varied. The data is presented in Table XXIII and reveals a trend of increasing Lp with increasing washing time, particularly at 20° C., and with increasing temperature. These numbers suggest that a convenient washing temperature and time for effective post-spin line washing could be about 60° C. overnight.

TABLE XXII

Process Parameters for Hollow Fiber Membrane 3000-1

| | Dope Pot | Dope Line | Bore Line | Spinerette | Quench Bath | Godet 1 | Bath 2 |
|---|---|---|---|---|---|---|---|
| Temperature (°C.) | 64 | 80.4 | 73.4 | 80.8 | 92 | 28 | 28 |

| | Intraannular Fluid | Extraannular Fluid | Take Up Rate (ft/min)[a] |
|---|---|---|---|
| Flow Rate (cm$^3$/min) | 65 | 12 | 17 |

TABLE XXII-continued

Process Parameters for Hollow Fiber Membrane 3000-1

| | Measurement | | | | |
|---|---|---|---|---|---|
| | 1 | 2 | 3 | Ave | std. dev. |
| Lp ($\times 10^{-9}$ cm$^3$/dyne sec) | 348 | 337 | 360 | 348 | 9 |

Also fiber production rate

Also, fiber production rate

TABLE XXIII

Results of Varying Wash Time and Temperatures After Taking the Fibers Off-Line

| Wash Temp. (°C.) | Wash Time (h) | Lp ($\times 10^{-9}$ cm$^3$/dyne sec)* |
|---|---|---|
| 20 | 4–5 | 277 |
| | 18–19 | 327 |
| | 92 | 412 |
| | 115.5 | 431 |
| | 139 | 432 |
| 40 | 15 | 379 |
| | 24 | 463 |
| | 87 | 478 |
| 55 | 8 | 497 |
| | 23 | 463 |
| 75 | 8 | 494 |
| | 23 | 485 |
| 90 | 8 | 436 |
| | 23 | 439 |

*Average from 2–7 test modules

6.10 Modification of Hollow Fiber Membranes

PES/PEO hollow fiber membranes are prepared as described in Example [Formerly 6.8]. Approximately 100 18-inch fiber membranes are placed in a two-liter beaker. The membranes are then washed with hot water at 95° C. for 16 h and then with 5N NaOH at 95° for 16 h in order to increase the number of available functional end groups. The fibers are then allowed to react with an 0.1N NaOH solution containing 10 wt % EGDGE at room temperature for 4 h. The fibers are then isolated and preferably washed with fresh cold water to remove unreacted EGDGE and excess base. Next, the samples are immersed in a 0.6N NaOH solution containing 2 wt % hydroxyethyl cellulose (HEC, Natrosol 250 JR, Aqualon Company, Wilmington, Del., USA) and heated to 60° C. for 16 h. Afterwards, the fibers are rinsed in 60° C. water to remove unbound components. This material is referred to as 1X HEC material. Additional layers of HEC may be incorporated onto the fibers by repeating the EGDGE and HEC treatments to give, as desired, 2X HEC, 3X HEC, 4X HEC, etc. materials.

The 3X HEC material is selected (although another HEC-layered material can be chosen) for further modification. The fibers are placed in a beaker and treated with an excess of an acetonitrile solution of 2 wt % 2-fluoro-1-methylpyridinium p-toluenesulfonate toulenesulfonate (FMP, Aldrich Chemical company, Milwaukee, Wis., USA) and 1 wt % triethylamine, at room temperature for about 15 min. The fibers are then washed with fresh acetontrile and air-dried.

A hollow polysulfone module with an internal volume of 1.5 mL is then packed with the FMP-activated fibers to give a final fiber membrane volume of 0.5 mL. Recombinant Protein A is then coupled to the contents of the module by recirculating a buffered solution of the protein through the module with the aid of a peristaltic pump. Any loosely-bound protein is washed off with sodium bicarbonate buffer and any unreacted FMP-activated groups are consumed by treating the fibers with 1 wt % mercaptoethanol in 30 mM sodium bicarbonate buffer. The module is then charged with a phosphate-buffered solution of human IgG. After washing off any loosely-bound material, the module is fond to elute 4.0 mg of IgG, giving a membrane capacity of 8.0 mg IgG/ml membrane volume.

Similarly, and aqueous solution of anti-Factor VIII (anti-FVIII, American Diagnositics, New York, N.Y., USA) in sodium bicarbonate buffer is recirculated through a module packed with FMP-activated fibers, as above, for 16 h at room temperature. Unreacted FMP-activated groups are extinguished similarly. A total of 22.9 mL of a FVIII solution (0.76 U/mL) in 0.015$\underline{M}$ citrate buffer (pH 7.0) containing 0.15$\underline{M}$ NaCl is then passed through the module at a rate of 2 mL/min. The module is then washed with a buffer of 0.015 $\underline{M}$ citrate and 0.15M NaCl until the absorbence at 280 nm of the washings is negligible, indicating the absence of protein in solution. The FVIII is then eluted with a suitable solution (e.g., an aqueous solution of 1$\underline{M}$ potassium iodide, 1$\underline{M}$ lysine, 20 $\underline{n}$M imidazole, and 5 $\underline{m}$M calcium chloride, pH 6.5). The eluate (3.8 mL) is found to contain 8.0 U of FVIII:C activity using a Stratchrom® FVIII:C Anti-Hemophilic Factor chromogenic Assay (Diagnostica Stage, 6 ter, rue Denis Papin, 92600 Asnieres, France), indicating a recovery of 46% based on the initial amount of FVIII loaded. Also, a purification factor of about 115 is achieved by this unoptimized procedure based on the specific activity of the initial FVIII solution.

6.11 A. Attachment of Anti-Factor IX Monoclonal Antibody to a 1.5 ml Module and Immunopurification of Factor IX Approximately 2.0 mg of anti-Factor IX monoclonal antibody was attached to a 1.5 mL FMP-activated hollow fiber affinity membrane module. A semipurified preparation of Factor IX (FIX) obtained from processed plasma was prepared for affinity purification in a Hepes buffered diluent containing 30 millimolar Mg++ to a calculated value of 10 Units of Factor IX per milliliter. A loading sample of 30 milliliters was applied to the anti-Factor IX module with a filtrate flow rate of 1.0 milliliter per minute. The loading volume was calculated to contain approximately 1.5 times the Factor IX that could be maximally bound to the module.

Factor IX was eluted from the module by applying a Hepes buffered aqueous solution without Mg++ in a total volume of 12 milliliters. The eluted fractions were measured for total protein by optical density at 280 nm using an ext. coeff. for pure Factor IX of 1.3 for 1 mg per milliliter in aqueous solution. Experimental results revealed a recovery average of 0.36 mgs total protein from the 1.5 ml module as measured by the ext. coeff. for Factor IX. (See Table I for results)

TABLE I

| EXPT # | FRACTION | AMT RECOV'D (mg) | AMT FIX AVAIL. |
|---|---|---|---|
| 1 | ELUATE | 0.44 | 1.5 |
| 2 | ELUATE | 0.28 | 1.5 |

The invention described and claimed herein is not meant to be limited in scope by above experiments. Indeed, various modifications of the invention in addition to those shown and described herein will become apparent to those skilled in the art from the foregoing description. Such modifications are also intended to fall within the scope of the appended claims.

We claim:

1. A method for carrying out affinity purification of a ligate in a hollow fiber membrane system comprising:
   (a) providing a ligate-containing liquid to a first side of at least one porous hollow fiber membrane with a ligand immobilized thereto, said membrane having a microporous structure, said liquid being under a pressure sufficient to cause a first portion of said liquid to flow convectively and tangentially across said first side of said membrane, and a second portion of said liquid being caused to flow convectively into and through said membrane emerging on a second side of said membrane, wherein said ligate present in said liquid binds to said ligand and is thereby separated from said liquid;
   (b) withdrawing said first portion of said liquid from said first side;
   (c) recirculating said first portion of said liquid to said first side of said membrane;
   (d) repeating steps (a) to (c) until a majority of said liquid has flowed into and through said membrane; and
   (e) providing an elution solution to one side of said membrane under a pressure sufficient to cause said elution solution to flow into and through said membrane and to effect the disassociation of any ligate-ligand bonds formed in step (a) wherein any ligate bound to said ligand is eluted with said elution solution.

2. The method of claim 1 wherein said ligate is IgG and said ligand is Protein A.

3. The method of claim 1 wherein said ligate is Factor VIII and the ligand is a monoclonal antibody to Factor VIII.

4. The method of claim 1 wherein said ligate is fibronectin and the ligand is porcine gelatin.

5. The method of claim 1 wherein said ligate is Factor IX and the ligand is a monoclonal antibody to Factor IX.

6. The method according to claim 1 wherein said porous hollow fiber membrane is at least 200 µm in thickness.

7. The method according to claim 1 wherein said porous hollow fiber membrane is a hydrophobic membrane having a derivatized interfacial area.

8. The method according to claim 1 wherein said ligand is selected from the group consisting of a surfactant, single strand nucleic acid, lectin, protein, carbohydrate, liposome, co-factor, derivatives and mixtures thereof.

9. The method according to claim 1 wherein said ligand is selected from the group consisting of glycoprotein, carrier protein, natural protein A, recombinant Protein A, Avidin and biotin.

10. The method according to claim 1 wherein said ligand is selected from the group consisting of monosaccharides, polysaccharides and heparin.

11. The method according to claim 1 wherein said ligand is an oligonucleotide or a polynucleotide.

12. The method according to claim 1 wherein said ligand is a monoclonal antibody or a polyclonal antibody.

13. The method according to claim 1 wherein said ligand is selected from the group consisting of animal cell surface receptor, plant cell surface receptor and bacterial cell surface receptor.

14. The method according to claim 1 wherein said ligand is an antibody against a molecule selected from the group consisting of immunoglobulin G, immunoglobulin M, immunoglobulin A, immunoglobulin E, tissue plasminogen activator, human interleukin protein, blood coagulation factor, human chorionic gonadotropin, thyrotropic hormone, carcinoembryonic antigen, α-feto protein, transforming growth factor, and interferon.

15. The method of claim 1 wherein said porous hollow fiber membrane is comprised of a hydrophobic polymer selected from the group consisting of polysulfones, polyethers, sulfones, polyimides, poly(arylene oxide), polyurethanes, poly(etheretherketones), polycarbonates, polyesters, poly(vinyl halides), and poly(vinylidene polyhalides), derivatives, blends, mixtures or copolymers thereof.

16. The method according to claim 1 wherein a plurality of said hollow fiber membranes are provided.

17. The method according to claim 1 wherein said ligand is selected from the group consisting of an enzyme, inhibitor, coagulation factor, hormone, histone, immunoglobulin, plasmid, derivatives and mixtures thereof.

18. The method according to claim 1 wherein said ligand is a polypeptide.

19. The method according to claim 1 wherein said ligand is an antigen.

20. The method according to claim 1 wherein said elution solution of step (e) is provided to the side of said membrane opposite to where said ligate-containing liquid was provided.

21. The method of claim 1, wherein the second portion of said liquid is withdrawable independently from said first portion.

22. The method of claim 1, further comprising the steps of:
   washing the membrane with a buffer solution under sufficient pressure to cause said solution to flow into and through said membrane; and
   providing a regeneration solution to the membrane under sufficient pressure to cause said solution to flow into and through said membrane to remove any residual elution solution from said membrane.

23. The method of claim 22, wherein the buffer solution and regeneration solution are provided to the second side of said membrane.

24. The method of claim 1, wherein said ligand is a carrier protein.

25. A method for carrying out affinity purification of a ligate in a hollow fiber membrane system comprising:
   (a) providing a ligate-containing liquid to a first side of at least one microporous hollow fiber membrane defining a membrane, said membrane having a ligand immobilized thereto, said liquid being under a pressure sufficient to cause a first portion of said liquid to flow convectively and tangentially across said first side of said membrane, with a second portion of said liquid being caused to flow convectively into and through said membrane emerging on a second side of said membrane, wherein said ligate present in said liquid binds to said ligand and is thereby separated from said liquid;
   (b) withdrawing said first portion of said liquid from said first side;
   (c) recirculating said withdrawn first portion of said liquid to said first side of said membrane;
   (d) repeating steps (a) to (c) until a majority of said liquid has flowed to the second side; and
   (e) providing an elution solution to one side of said membrane under a pressure sufficient to cause said elution solution to flow into and through said membrane and to effect the disassociation of any ligate-ligand bonds, wherein any ligate bound to said ligand is eluted with said elution solution.

26. An apparatus for carrying out affinity separation comprising:

at least one porous hollow fiber membrane having a ligand immobilized thereto;

means for enclosing said at least one porous hollow fiber membrane;

means for providing a fluid in intimate contact with a first side of said enclosed porous hollow fiber membrane;

first exit means for directing into a first container any fluid present on a second side of said enclosed porous hollow fiber membrane opposite the first side to which said fluid is first provided according to the fluid providing means; and second exit means for directing said fluid present on the first side of said membrane into a second container, wherein at least part of said fluid leaving from said first exit means has originated from said fluid providing means and said hollow fiber membrane has a substantially isotropic microporous structure in all directions throughout the membrane, with pores large enough to permit convective flow of macromolecule-containing solutions across the hollow fiber membrane.

27. The apparatus of claim 26, wherein said membrane has a pore size of at least 0.2 microns.

28. The apparatus of claim 26, wherein said membrane is at least about 200 microns in thickness.

29. The apparatus of claim 26, wherein said means for enclosing said hollow fiber membrane has an inner volume ranging from about 1 Ml to about 10 L.

30. The apparatus of claim 26, wherein said fluid providing means is a pump.

* * * * *

UNITED STATES PATENT AND TRADEMARK OFFICE
CERTIFICATE OF CORRECTION

PATENT NO. : 5,683,916

DATED : November 4, 1997

INVENTOR(S) : GOFFE et al.

It is certified that error appears in the above-identified patent and that said Letters Patent is hereby corrected as shown below:

Column 49, claim 9, lines 2-3, delete "carrier protein,".

Signed and Sealed this

Twenty-sixth Day of May, 1998

Attest:

BRUCE LEHMAN

Attesting Officer     Commissioner of Patents and Trademarks